(12) United States Patent
Partain

(10) Patent No.: US 8,320,518 B2
(45) Date of Patent: *Nov. 27, 2012

(54) METHODS, APPARATUS, AND COMPUTER-PROGRAM PRODUCTS FOR INCREASING ACCURACY IN CONE-BEAM COMPUTED TOMOGRAPHY

(75) Inventor: Larry Partain, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/209,323

(22) Filed: Aug. 12, 2011

(65) Prior Publication Data

US 2011/0299652 A1    Dec. 8, 2011

Related U.S. Application Data

(63) Continuation of application No. 12/360,795, filed on Jan. 27, 2009, now Pat. No. 8,009,794.

(60) Provisional application No. 61/024,903, filed on Jan. 30, 2008.

(51) Int. Cl.
*A61B 6/03* (2006.01)
*H05G 1/64* (2006.01)
*G21K 1/04* (2006.01)

(52) U.S. Cl. ............... 378/7; 378/19; 378/150; 378/152

(58) Field of Classification Search .................. 378/6, 7, 378/19, 150, 152

See application file for complete search history.

(56) References Cited

U.S. PATENT DOCUMENTS

| | | | |
|---|---|---|---|
| 4,182,311 A | 1/1980 | Seppi et al. | |
| 4,995,107 A * | 2/1991 | Klingenbeck | 378/7 |
| 5,640,436 A | 6/1997 | Kawai et al. | |
| 6,173,032 B1 | 1/2001 | Besson | |
| 6,246,742 B1 | 6/2001 | Besson et al. | |
| 6,470,067 B1 * | 10/2002 | Harding | 378/19 |
| 6,480,565 B1 | 11/2002 | Ning | |
| 6,501,828 B1 | 12/2002 | Popescu | |
| 6,504,892 B1 | 1/2003 | Ning | |
| 6,542,573 B2 | 4/2003 | Schomberg | |
| 6,639,964 B2 * | 10/2003 | Schneider et al. | 378/7 |
| 6,744,845 B2 * | 6/2004 | Harding et al. | 378/16 |
| 6,856,666 B2 | 2/2005 | Lonn et al. | |
| 7,113,569 B2 | 9/2006 | Okumura et al. | |
| 7,206,383 B2 | 4/2007 | Zhao et al. | |
| 7,336,760 B2 * | 2/2008 | Virshup et al. | 378/7 |
| 7,418,073 B2 * | 8/2008 | Schlomka et al. | 378/6 |
| 7,455,453 B2 | 11/2008 | Lauritsch et al. | |
| 7,474,728 B2 * | 1/2009 | Schlomka et al. | 378/6 |
| 7,515,678 B2 | 4/2009 | Hsieh et al. | |
| 7,551,709 B2 * | 6/2009 | Schlomka et al. | 378/6 |
| 7,580,499 B2 * | 8/2009 | Van Stevendaal et al. | 378/7 |
| 7,590,215 B2 * | 9/2009 | Schlomka | 378/4 |
| 7,715,520 B2 | 5/2010 | Nagata et al. | |

* cited by examiner

*Primary Examiner* — Allen C. Ho
(74) *Attorney, Agent, or Firm* — Kilpatrick Townsend & Stockton LLP

(57) ABSTRACT

Portions of the radiation source are obscured so that the radiation only passes through the specific areas of the patient related to the regions-of-interest to the doctor. Scattered radiation received by detector pixels that are obscured by direct-line of sight radiation are used to estimate the scattered radiation in the un-obscured portion, which can be used to increase the accuracy of the image taken through the un-obscured portion.

18 Claims, 14 Drawing Sheets

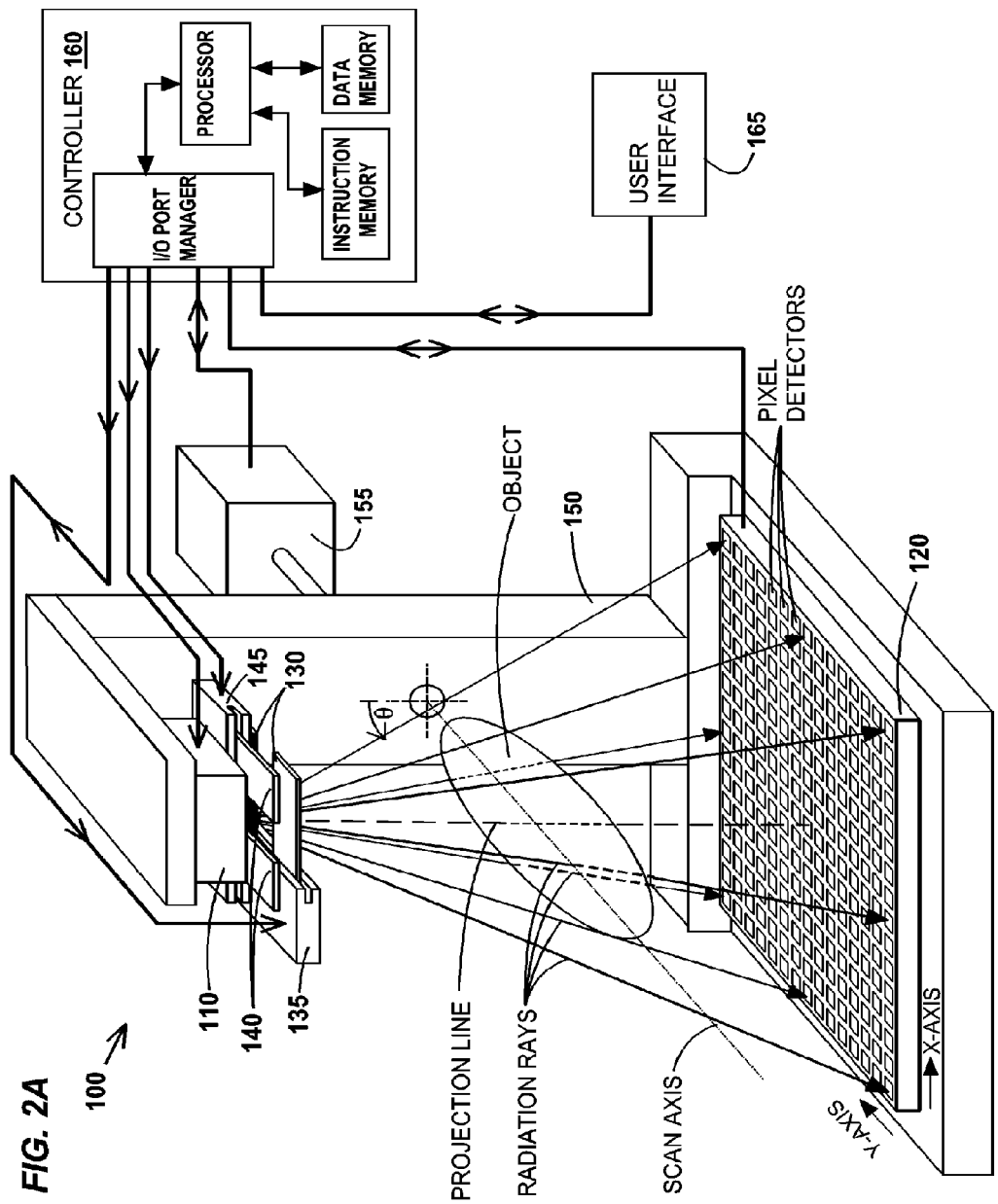

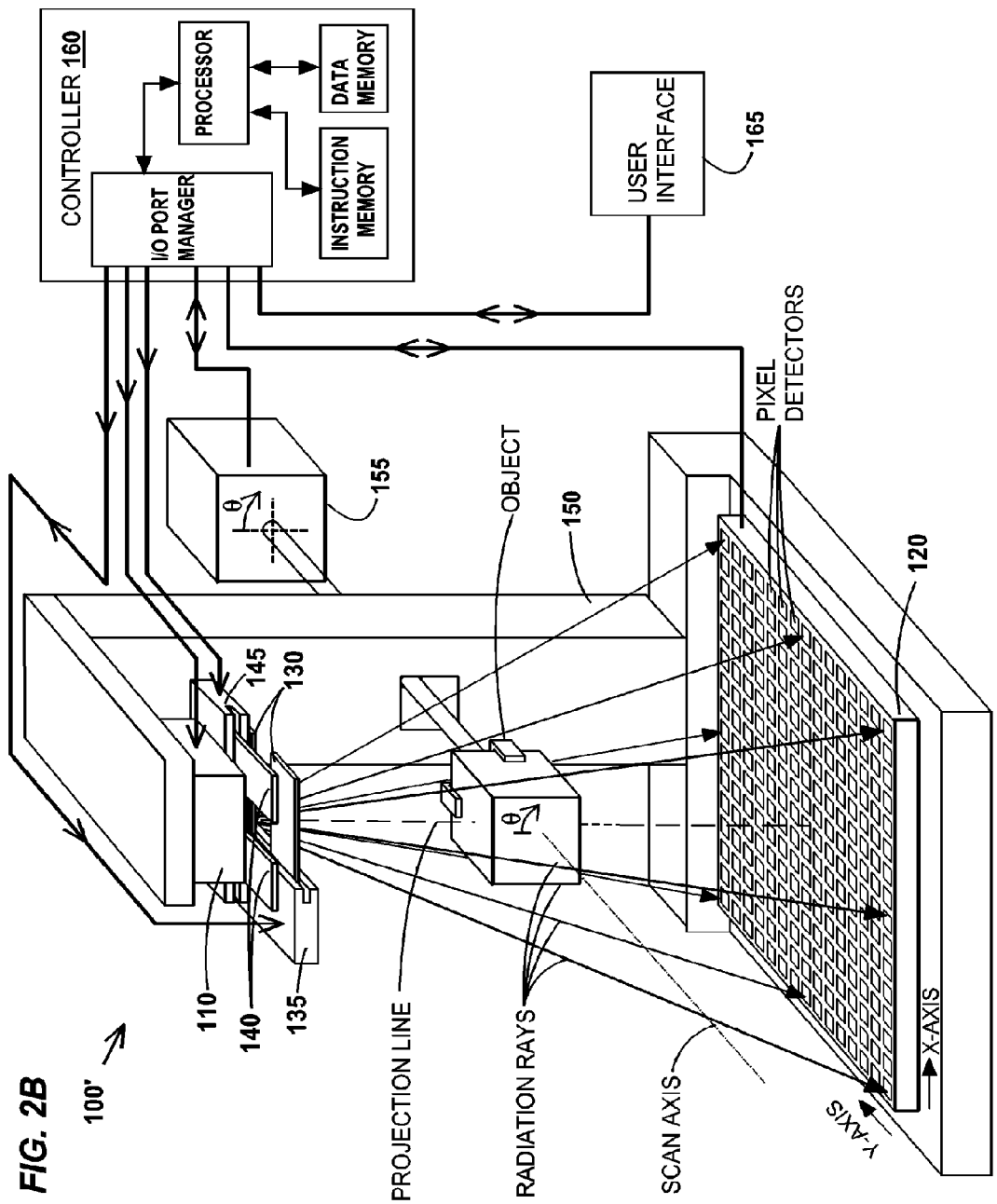

METHODS, APPARATUS, AND COMPUTER-PROGRAM PRODUCTS FOR INCREASING ACCURACY IN CONE-BEAM COMPUTED TOMOGRAPHY

CROSS-REFERENCES TO RELATED APPLICATIONS

This application is a Continuation of U.S. patent application Ser. No. 12/360,795, filed Jan. 27, 2009, now issued as U.S. Pat. No. 8,009,794, entitled "METHODS, APPARATUS, AND COMPUTER-PROGRAM PRODUCTS FOR INCREASING ACCURACY IN CONE-BEAM COMPUTED TOMOGRAPHY," which claims benefit under 35 USC 119(e) of U.S. Provisional Patent Application No. 61/024,903, filed Jan. 30, 2008, both of which are incorporated herein by reference in their entirety for any and all purposes.

BACKGROUND OF THE INVENTION

Cone beam (CB) computed tomography (CT) involves the imaging of the internal structure of an object by collecting several projection images ("radiographic projections") in a single scan operation ("scan"), and is widely used in the medical field to view the internal structure of selected portions of the human body as well as in the industrial and security fields to perform non-destructive inspection and to detect contraband and weapons in security screening. Typically, several two-dimensional projections (which are images) are made of the object, and a three-dimensional representation of the object is constructed from these projections using various tomographic reconstruction methods. From the three-dimensional data sets, conventional CT slice images through the object can be generated. The two-dimensional projections are typically created by transmitting radiation from a "point source" through the object, which will absorb some of the radiation based on its size and density, and collecting the non-absorbed radiation onto a two-dimensional imaging device, or imager, which comprises an array of pixel detectors (simply called "pixels"). Such a system is shown in FIG. 1. Typically, the point source and the center of the two-dimensional imager lie on a common axis, which may be called the projection axis. The source's radiation emanates toward the imaging device in a volume of space approximately defined by a right-circular cone, with roughly circular- or ellipse-shaped cross sections perpendicular to the axis (where deviations are caused by non-ideal aspects that include the heel effect in X-ray sources), having its vertex at the point source and its base at the imaging device. This is the reason the radiation is often called cone-beam (CB) radiation. The imagers in state-of-the-art CBCT systems measure around 30 cm by 40 cm, having approximately 750 rows of pixels with approximately 1,000 pixels in each row, for approximately 750,000 pixels. Generally, when no object is present within the cone, the distribution of radiation is substantially uniform on any roughly circular or elliptical area on the imager that is centered about the projection axis, and that is within the cone. However, the shape of the radiation boundary on the imager may be non-uniform, from a large number of perturbations, so that there is no perfect rotational symmetry about the projection axis. In any event, any non-uniformity in the distribution can be measured in a calibration step and accounted for. The projection axis may not be at the center of the imager or the center of the object. It may pass through them at arbitrary locations including very near the edge.

In an ideal imaging system, rays of radiation travel along respective straight-line transmission paths from the source, through the object, and then to respective pixel detectors without generating scattered rays. However, in real systems, when photons of X-radiation in rays interact with a portion of the object (including photoelectric, Compton and pair production interactions), one or more scattered rays are often generated that deviate from the transmission path of the incident radiation. These scattered rays are often received by "surrounding" pixel detectors that are not located on the transmission path that the initial photon-containing-rays of radiation was transmitted on, thereby creating errors in the electrical signals of the surrounding pixel detectors. Also, in typical two-dimensional imagers, the radiation meant to be received by a pixel is often scattered by various components of the source-imager system (e.g., scintillation plate, bow tie filters, radiation hardening filters, the metal anode that electrons hit in the source to produce X-rays etc.), and received by surrounding pixels. These effects are often characterized, in part, by a point-spread function (PSF), which is a two-dimensional mapping of the amount of error caused in surrounding pixels by a given amount of radiation intended for a central pixel. The surface of the PSF is similar to the flared shape of a trumpet output, with the greatest amount of error occurring in pixels adjacent to the central pixel.

Each of the above non-ideal effects creates spatial errors in the pixel data generated by the two-dimensional imager. In turn, the spatial errors cause artifacts (e.g., phantom images) and loss of resolution and contrast and blurring in the CBCT image slices produced by the radiation imaging system.

BRIEF SUMMARY OF THE INVENTION

As part of making his inventions, the inventor has recognized that, while radiologists and physicians use CBCT imaging to obtain broad images of a patient's torso during the initial portion of the diagnostic phase, they often focus their attention to specific areas of the images, such as to parts of specific organs, during the latter portion of the diagnostic phase and/or treatment phase. As also part of making his inventions, the inventor has discovered that the accuracy of the images generated from CBCT can be greatly improved by obscuring portions of the radiation source so that the radiation only passes through the specific areas of the patient related to the regions-of-interest to the doctor. The obscuring action causes less radiation to pass through the patient's body, which in turn causes the radiation to undergo less scattering through the patient's body, thus reducing a major source of error in the image accuracy. The obscuring action may be performed with bodies of material that absorb at least 60 percent of the incident radiation (and up to 100 percent); total absorption of the incident radiation is not necessary although it is sometimes preferred. Thus, as used herein, the action of obscuring a portion of a radiation beam means absorbing at least 60 percent of the incident radiation, or initial value, of that portion, and up to 100 percent thereof. The obscuring action also causes the radiation to strike a smaller portion of the two-dimensional imager. The use of less than the full area of the two-dimensional imaging device is contrary to conventional wisdom and practice in the art, which teaches artisans, physicians, and radiologists to use the full extent of the two-dimensional imager. For this reason, the prior art teaches against the present invention. The obscuring action may be done along either or both of the axial and trans-axial dimensions of the imager (the axial dimension is parallel to the rotation axis of the gantry, and the trans-axial dimension is perpendicular to the axial dimension). If the obscuring action is only done along the axial dimension, then standard 3-D reconstruction methods may be used; this is often the preferred manner of obscuring the beam. If the obscuring action is done along the trans-axial dimension (also called the lateral dimension), then truncated 3-D reconstruction methods may be used to just reconstruct limited volumes of the object being imaged. In further preferred implementations of the present inventions, an estimate of the scattered radiation may be generated from the measured pixel data of selected pixels that lie outside of the illuminated area. The scatter estimate may be subtracted from, or otherwise factored out of, the CT data set to further improve the accuracy of the data.

A first general invention of the present application is directed to a method of operating a cone-beam CT scanning system, the system having a two-dimensional pixel array with a number Xpix of pixels in a first dimension that is perpendicular to the system's axis of rotation and a number Ypix of pixels in a second dimension that is parallel to the system's axis of rotation, Xpix being greater than one hundred and Ypix being greater than ten. The system further has a source of radiation that emits a cone-beam of radiation that normally covers all of the pixels of the pixel array. Broadly stated, the method comprises positioning an object between the source of radiation and the pixel array, obscuring a portion of the cone beam of radiation such that direct rays of the radiation cover less than 85 percent of the area of the pixel array and span at least three percent of the second dimension in a portion of the pixel array, and obtaining a plurality of projections of the object with the cone beam obscured, the plurality of projections being taken at a corresponding plurality of relative angles between the object and the source of radiation. The obscuring action may be done by placing a collimator (e.g., one or more sets of fan blades) between the radiation source and the object.

A second general invention of the present application is directed to a method of operating a cone-beam CT scanning system, the system having a two-dimensional pixel array with a number Xpix of pixels in one of the dimensions and a number Ypix of pixels in the other dimension, Xpix being greater than one hundred and Ypix being greater than ten. The system further has a source of radiation that emits a cone-beam of radiation that normally covers all of the pixels of the pixel array. Broadly stated, the method comprises determining an extent of the pixel array that will receive direct-path radiation passing through a target volume of the object during a rotational scan of the object, the rotation scan including a plurality of projections of the object taken at a corresponding plurality of relative angles between the object and the source of radiation, the extent of the angles being equal to or greater than 180 degrees, and the target portion being smaller than the size of the object. The method further comprises obscuring a portion of the cone beam of radiation such that direct rays of the radiation cover at least the determined extent, but less than 85 percent of the pixel array. The obscuring action may be done by placing a collimator (e.g., one or more sets of fan blades) between the radiation source and the object. Further embodiments of the method may include obtaining a plurality of projections of the object with the cone beam obscured, the plurality of projections being taken at a corresponding plurality of relative angles between the object and the source of radiation.

A third general invention of the present application is directed to a method of operating a cone-beam CT scanning system, the system having a two-dimensional pixel array with a number Xpix of pixels in a first dimension that is perpendicular to the system's axis of rotation and a number Ypix of pixels in a second dimension that is parallel to the system's axis of rotation, Xpix being greater than one hundred and Ypix being greater than ten. The system further has a source of radiation that emits an un-obscured cone-beam of radiation that normally covers all of the pixels of the pixel array. Broadly stated, the method comprises obtaining a first scan of the object with the direct rays of the radiation covering at least 85 percent of the pixel array; and obtaining a second scan of the object with the direct rays of the radiation covering less than 85 percent of the pixel array and spanning at least three percent of the second dimension in a portion of the pixel array. Further preferred embodiments of this method may include generating a three-dimensional CT data set of the object from the projections of the scans using a truncated reconstruction method. A related computer-program product invention may comprise acquiring the sets of radiographic projections of these two scans and generating a three-dimensional CT data set of the object with a truncated reconstruction method.

A fourth general invention of the present application is directed to a method of reconstructing projection data comprising acquiring a set of radiographic projections of an object that has been taken with a portion of the pixels being obscured from the cone-beam radiation, acquiring an indication of which pixels have been obscured, and performing a truncated reconstruction of the object using the radiographic projection and the indication of which pixels have been obscured. The action of acquiring the sets of radiographic projections may comprise receiving the sets from another entity or process, and may comprise instructing a cone-beam CT scanning system to generate the sets. The action of acquiring the indication of which pixels have been obscured may comprise receiving the indication from another entity or process, and may comprise analyzing the pixel values of the scans to determine which pixels have been obscured. Further preferred embodiments of this method may include generating estimates of scattered radiation from the data of the obscured pixels and generating corrected radiographic projections from the acquired radiographic projections and the estimates of the scattered radiation. A related computer-program product invention comprises instruction sets that direct a data processor to perform the above actions.

A fifth general invention of the present application is directed to a method of processing projection data comprising acquiring a set of radiographic projections of an object that have been taken with a portion of the pixels being obscured from the cone-beam radiation, obtaining an indication of which pixels have been obscured, and generating estimates of scattered radiation from the values of the obscured pixels. The action of acquiring the sets of radiographic projections may comprise receiving the sets from another entity or process, and may comprise instructing a cone-beam CT scanning system to generate the sets. The action of acquiring the indication of which pixels have been obscured may comprise receiving the indication from another entity or process, and may comprise analyzing the pixel values of the scans to determine which pixels have been obscured. Further preferred embodiments of this method may include generating corrected projections from the radiographic projections and the estimates of the scattered radiation. A related computer-program product invention comprises instruction sets that direct a data processor to perform the above steps.

A sixth general invention of the present application is directed to a cone-beam CT scanning apparatus. Broadly stated, the apparatus comprises a two-dimensional pixel array with a number Xpix of pixels in an axial dimension and a number Ypix of pixels in a trans-axial dimension, Xpix being greater than one hundred and Ypix being greater than ten, a source of radiation that emits a cone-beam of radiation that normally covers all of the pixels of the pixel array, a collimator disposed closer to the source of radiation than the two-dimensional pixel array and that is selectively moveable to obscure at least one portion of the cone-beam, a first positioner that positions the collimator in response to a first set of at least one control signal, and a controller that generates the first set of at least one control signal. In one preferred embodiment, the collimator comprises a first set of fan blades that are selectively moveable to obscure one or both sides of the cone-beam, and the first positioner positions the first set of fan blades in response to the first set of at least one control signal. The edges of the fan blades of the first set are oriented substantially perpendicular to the scan axis, and are substantially parallel with the trans-axial dimension of the imaging device. With this configuration of this preferred embodiment, the first set of fan blades can selectively obscure pixels in the axial (Ypix) dimension. Further preferred embodiments further comprise a second set of fan blades that are selectively moveable to obscure one or both sides of the cone-beam along the trans-axial dimension, and a second positioner that positions the second set of fan blades in response to a second set of at least one control signal, wherein the controller further generates the second set of at least one control signal. In this further preferred embodiment, the edges of the fan blades of the second set are oriented substantially parallel to the scan axis, and are substantially perpendicular to the axial dimension of the imaging device.

The obscuring of the cone beam according to the present invention reduces the field of view of the image, but improves image accuracy in the field of view. A reconstructed three-dimensional CT data set models the radiation attenuation coefficient of the object's material at a three dimensional array of locations, called voxels (which is shorthand for "volume pixels"). As a ray of radiation passes through the voxels of the object, its intensity decreases exponentially along the beam path. It is the small differences in the attenuation coefficients of the voxels that produce the subtle contrasts that physicians and radiologists use to image, identify, and diagnose problems. When there is a lot of scattering of the radiation rays, there is a lot of noise in the projection data, and this noise decreases the accuracy of reconstructing, and thereby measuring, each voxel's attenuation coefficient. The scattered radiation represents noise because it has been generated at unknown points in the object being imaged, and has been attenuated by unknown materials along unknown paths through the object. As part of making his invention, the inventor has recognized that scattered radiation generated at a point of the object can be dispersed over a wide area of the pixel array. The present invention reduces the overall magnitude of the scattered radiation by decreasing radiation in areas where it is not needed for the physicians and radiologists to see the subtle contrasts that they seek to examine. The improvement in the imaging quality results in more accurate Hounsfield units for the voxels. A Hounsfield unit is essentially a rescaling of the attenuation coefficient of a voxel, where a Hounsfield unit value of 0 represents the attenuation coefficient of water, and a Hounsfield unit value of −1000 represents the attenuation coefficient of air. Voxels that are more dense than water have Hounsfield units that are greater than zero, and materials that are less dense than water have Hounsfield units that are less than zero. The Hounsfield unit system provides physicians and radiologists with higher contrast perspective to see finer details since the human body is mostly water. The present inventions improve the accuracy of measured Hounsfield units by reducing radiation scattering and reducing the field of view.

These and other inventions are described below in greater detail. The inventions disclosed herein may be used separately to together in various combinations, and one or more elements and features of each invention may be used in the other inventions.

BRIEF DESCRIPTION OF THE DRAWINGS

FIG. 2A is a schematic diagram of a first exemplary embodiment of a radiation imaging system according to a first invention of the present application.

FIG. 2B is a schematic diagram of a second exemplary embodiment of a radiation imaging system according to a first invention of the present application.

DETAILED DESCRIPTION OF THE INVENTION

Figure 1:
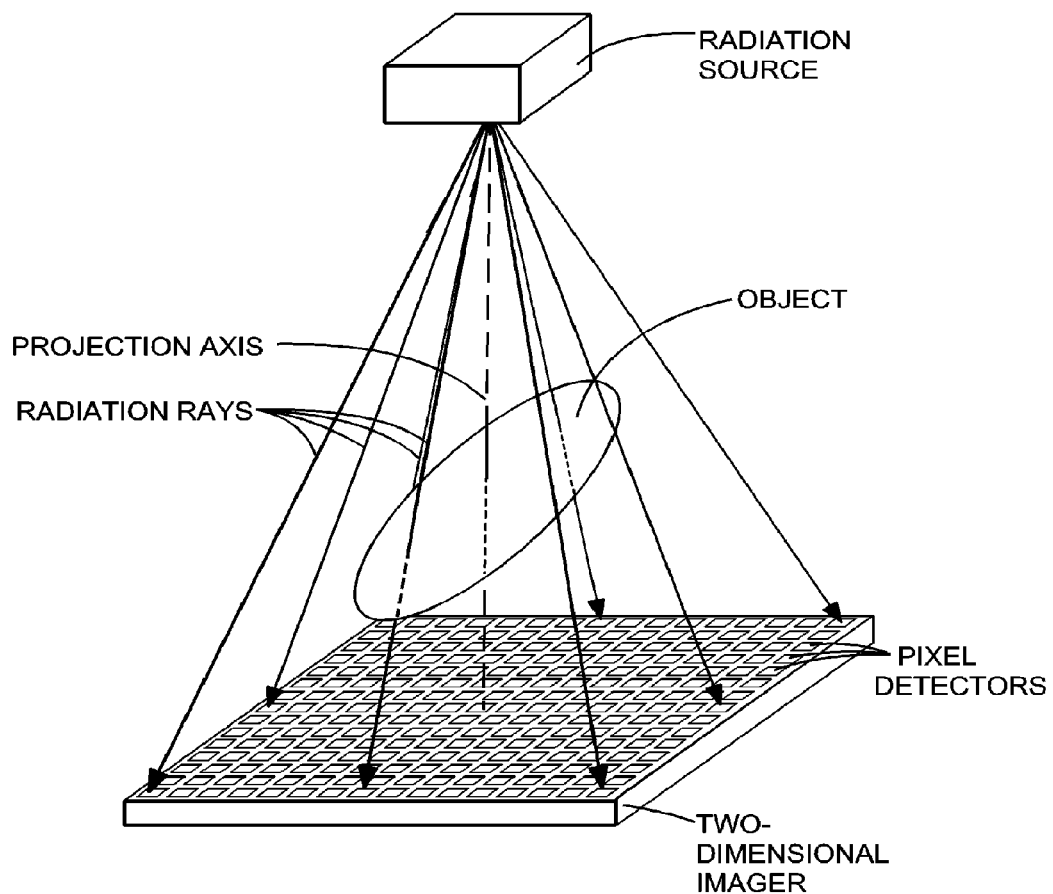
FIG. 1 is a schematic diagram of a radiation imaging system according to the prior art.

The inventions of the present application will be described more fully hereinafter with reference to the accompanying drawings, in which exemplary embodiments of the inventions are shown. This inventions may, however, be embodied in different forms and should not be construed as limited to the embodiments set forth herein. Rather, these embodiments are provided so that this disclosure is thorough and complete and fully conveys the scope of the inventions to one skilled in the art. In the drawings, the relative dimensions of some elements may be exaggerated for clarity. The same reference numerals are used to denote the same elements throughout the specification. The elements may have different interrelationships and different positions for different embodiments.

The terms used herein are for illustrative purposes of the present inventions only and should not be construed to limit the meaning or the scope of the present inventions. As used in this specification, a singular form may, unless definitely indicating a particular case in terms of the context, include a plural form. Also, the expressions "comprise" and/or "comprising" used in this specification neither define the mentioned characteristics, numbers, steps, actions, operations, members, elements, and/or groups of these, nor exclude the presence or addition of one or more other different characteristics, numbers, steps, operations, members, elements, and/or groups of these, or addition of these. Spatially relative terms, such as "over," "above," "upper," "under," "beneath," "below," "lower," and the like, may be used herein for ease of description to describe one element or feature's relationship to another element(s) or feature(s) as illustrated in the figures. It will be understood that the spatially relative terms are intended to encompass different orientations of an apparatus in use or operation in addition to the orientation depicted in the figures. For example, if an apparatus in the figures is turned over, elements described as "below" or "beneath" or "under" other elements or features would then be oriented "over" or "above" the other elements or features. Thus, the exemplary term "above" may encompass both an above and below orientation.

As used herein, terms such as "first," "second," etc. may be used to describe one or more members, components, characteristics, etc. However, it is obvious that the members, components, characteristics, etc. should not be defined by these terms. The terms are used only for distinguishing one member, component, characteristic, etc. from another. Thus, a first member, component, characteristic, etc. that is described may also refer to a second member, component, characteristic, etc. without departing from the scope of the present invention.

System Overview. FIG. 2A is a schematic diagram of a first exemplary imaging system 100 according to the system inventions of the present application. System 100 comprises a radiation source 110, a two-dimensional imaging device 120 disposed opposite to radiation source 110 along a projection line, a first set of fan blades 130 disposed between the radiation source and the two-dimensional imaging device, a first fan-blade drive 135 that holds fan blades 130 and sets their positions. The edges of fan blades 130 are oriented substantially perpendicular to the scan axis (defined below), and are substantially parallel with the trans-axial dimension (defined below) of imaging device 120. As an option, system 100 may further comprise a second set of fan blades 140 disposed between the radiation source and the two-dimensional imaging device, and a second fan-blade drive 145 that holds fan blades 140 and sets their positions. The edges of fan blades 140 are oriented substantially parallel with the scan axis (defined below), and are substantially parallel to the axial dimension (defined below) of imaging device 120. The fan blades are examples of a collimator, and are disposed closer to radiation source 110 than imaging device 120. Examples of other collimators are provided below. System 100 further comprises a gantry 150 that holds radiation source 110, imaging device 120, and fan-blade drives 135 and 145 in fixed or known spatial relationships to one another, a mechanical drive 155 that rotates gantry 150 about an object disposed between radiation source 110 and imaging device 120, with the object being disposed between fan blades 130 and 140 on the one hand, and imaging device 120 on the other hand. The term gantry has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown. These components do not form part of the present inventions. Also not shown is a support table for the object (i.e., an object support member), which does not form a part of the present inventions related to System 100. Additionally, system 100 further comprises a controller 160 and a user interface 165, with controller 160 being electrically coupled to radiation source 110, mechanical drive 155, fan-blade drives 135 and 145, imaging device 120, and user interface 165. User interface 165 provides a human interface to controller 160 that enables the user to at least initiate a scan of the object, to collect measured projection data from the imaging device, and to adjust the positions of fan blades 130 and 140. User interface 165 may be configured to present graphic representations of the measured data.

In imaging system 100, gantry 150 is rotated about the object during a scan such that radiation source 110, fan blades 130 and 140, fan-blade drives 135 and 145, and two-dimensional imaging device 120 circle around the object. More specifically, gantry 150 rotates these components about a scan axis, as shown in the figure, where the scan axis intersects the projection line, and is typically perpendicular to the projection line. The object is aligned in a substantially fixed relationship to the scan axis. The construction provides a relative rotation between the projection line on the one hand and the scan axis and an object aligned thereto on the other hand, with the relative rotation being measured by an angular displacement value $\theta$. Mechanical drive 155 is mechanically coupled to gantry 150 to provide rotation upon command by controller 160. The two-dimensional imaging device comprises a two-dimensional array of pixels that are periodically read to obtain the data of the radiographic projections. Imaging device 120 has an X-axis and a Y-axis, which are perpendicular to each other. Imaging device 120 is oriented such that its Y-axis is parallel to the scan axis. For this reason, the Y-axis is also referred to as the axial dimension of imaging device 120, and the X-axis is referred to as the trans-axial dimension, or lateral dimension, of device 120. The X-axis is perpendicular to a plane defined by the scan axis and the projection line, and the Y-axis is parallel to this same plane. Each pixel is assigned a discrete X-coordinate ("X") along the X-axis, and a discrete Y-coordinate ("Y") along the Y-axis. In typical implementations, the size of the array is 1024 pixels by 768 pixels, with the longer dimension of the array being oriented parallel to the X-axis. As used herein, the discrete X-coordinates start at 1 and end at Xpix (e.g., Xpix=1024), and the discrete Y-coordinates start at 1 and end at Ypix (e.g., Ypix=768). A smaller number of pixels are shown in the figure for the sake of visual clarity. The imaging device may be centered on the projection line to enable full-fan imaging of the object, may be offset from the projection line to enable half-fan imaging of the object, or may be movable with respect to the projection line to allow both full-fan and half-fan imaging of objects. As an example of a half-fan configuration, the imaging device may be offset from the center by 16 centimeters in its X-dimension when the imaging device has a span in the X dimension of 40 centimeters.

Figure 3:
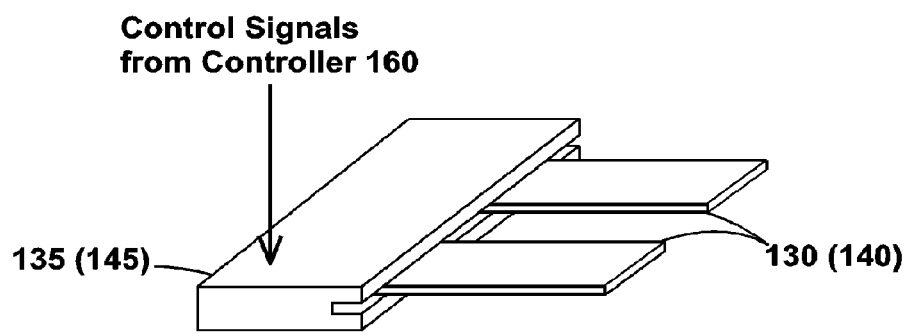
FIGS. 3 and 4 are perspective views of exemplary implementations of a fan blade and a fan-blade drive according to a first invention of the present application.

FIG. 3 shows a perspective view of a first exemplary implementation of fan blades 130 and fan-blade drive 135. Each fan blade 130 may have a thin rectangular shape, and may comprise a material that absorbs the radiation of source 110. Such a material may comprise lead (Pb). Each fan blade 130 absorbs at least 60% of the incident radiation from radiation source 110. In preferred implementations, a fan blade absorbs at least 90 percent, and more preferably at least 99 percent, of the radiation incident upon it. Fan-blade drive 135 may comprise two mechanical positioners. In one exemplary implementation, each mechanical positioner is mechanically coupled to a respective fan blade to cause the fan blade to move in a controlled and measurable (e.g., predictable) manner. In another implementation, one of the mechanical positioners is mechanically coupled to the fan blades to cause the blades to move relative to one another so as to vary the distance of the gap between the blades in a controlled and measurable manner, and the other positioner is mechanically coupled to the blades to cause the blades to move as a group in a controlled and measurable manner. In the latter exemplary implementation, the first positioner and the fan blades may be mechanically disposed on a carriage, and the second positioner may be mechanically coupled to the carriage. Each positioner may comprise a linear motor servo, a rotating motor servo with rotation-to-linear translation mechanism, or the like. The construction of fan blades 140 and fan blade drive 145 may be the same as that of fan blades 130 and fan-blade drive 135, respectively.

Figure 4:
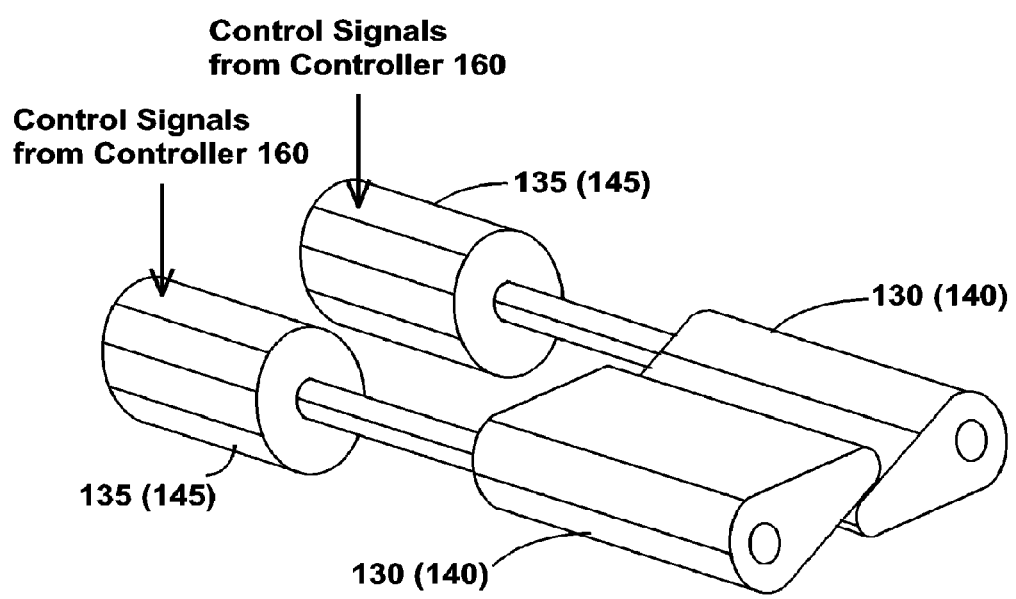

FIG. 4 shows a perspective view of a second exemplary implementation of fan blades 130 and fan-blade drive 135. Each fan blade 130 may comprise an eccentric cam, and may comprise a material that absorbs at least 60% of the incident radiation from radiation source 110. Such a material may comprise lead (Pb). In preferred implementations, a fan blade absorbs at least 90 percent, and more preferably at least 99 percent, of the radiation incident upon it. Each fan-blade drive 135 may comprise a rotating servo motor, preferably with a set of reduction gears, which drives the eccentric cam. Fan blades 130 may be placed in an overlapping relationship so that each may obscure more than 50% of imaging device 120. The construction of fan blades 140 and fan blade drive 145 may be the same as that of fan blades 130 and fan-blade drive 135, respectively. As used herein, the term "fan blades" has broad meaning, and covers all configurations of structural members that can provide a primary region (e.g., gap, aperture, etc.) through which radiation may pass with relatively little attenuation compared to one or more surrounding regions, and where a dimension of the primary region may be controlled and/or where the primary region may be selectively disposed toward or away from the projection line so that the primary region can be selectively disposed inside or outside of the source's radiation field that is collected by the imaging device. Also as used herein, the terms "fan-blade drive" and "positioners" have broad meanings, and cover all configurations of electro-mechanical elements that can provide the above positioning of the fan blades and other collimators.

Figure 5:
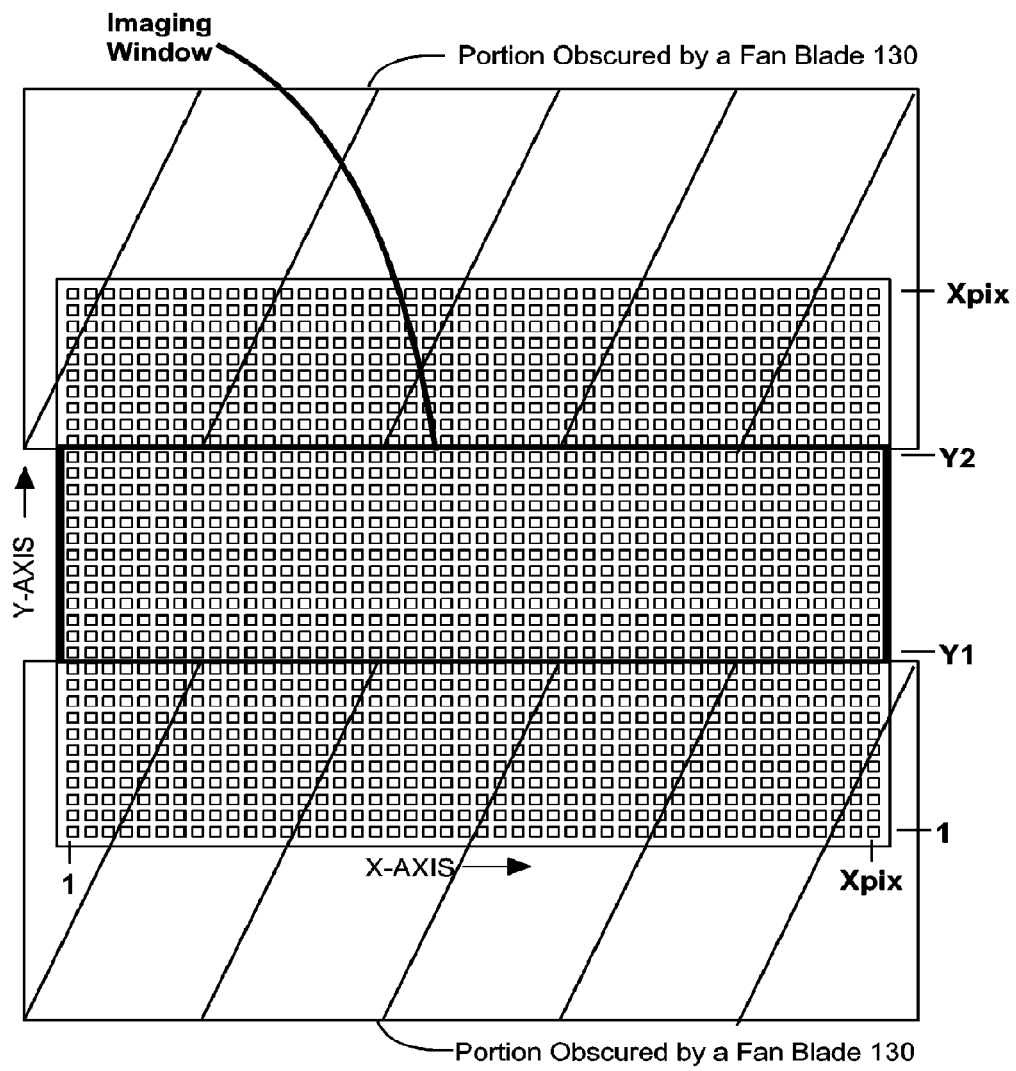
FIGS. 5-7 are top plan views of the imaging device showing the obscured portions caused by the fan blades according to the present invention.
Figure 6:
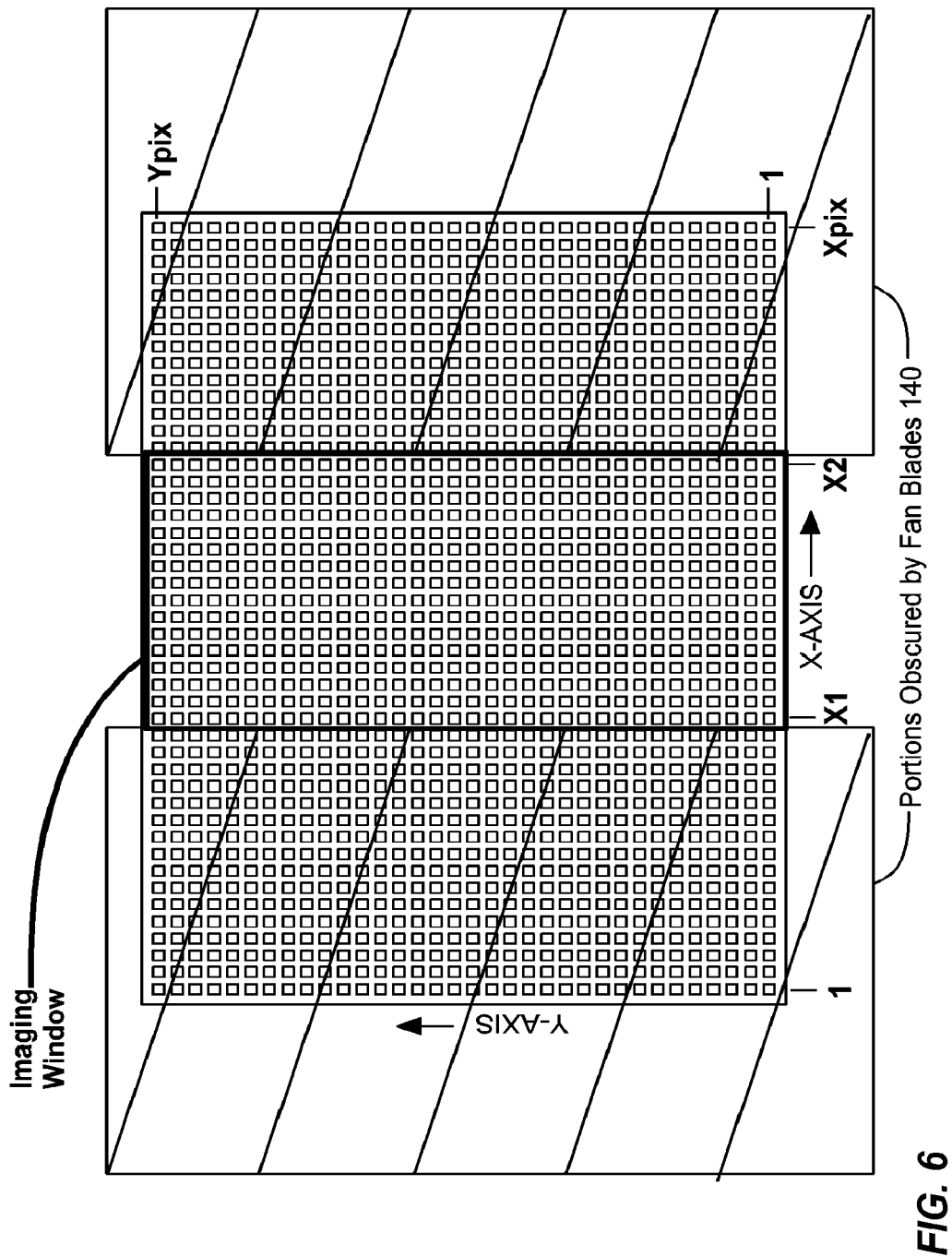
Figure 7:
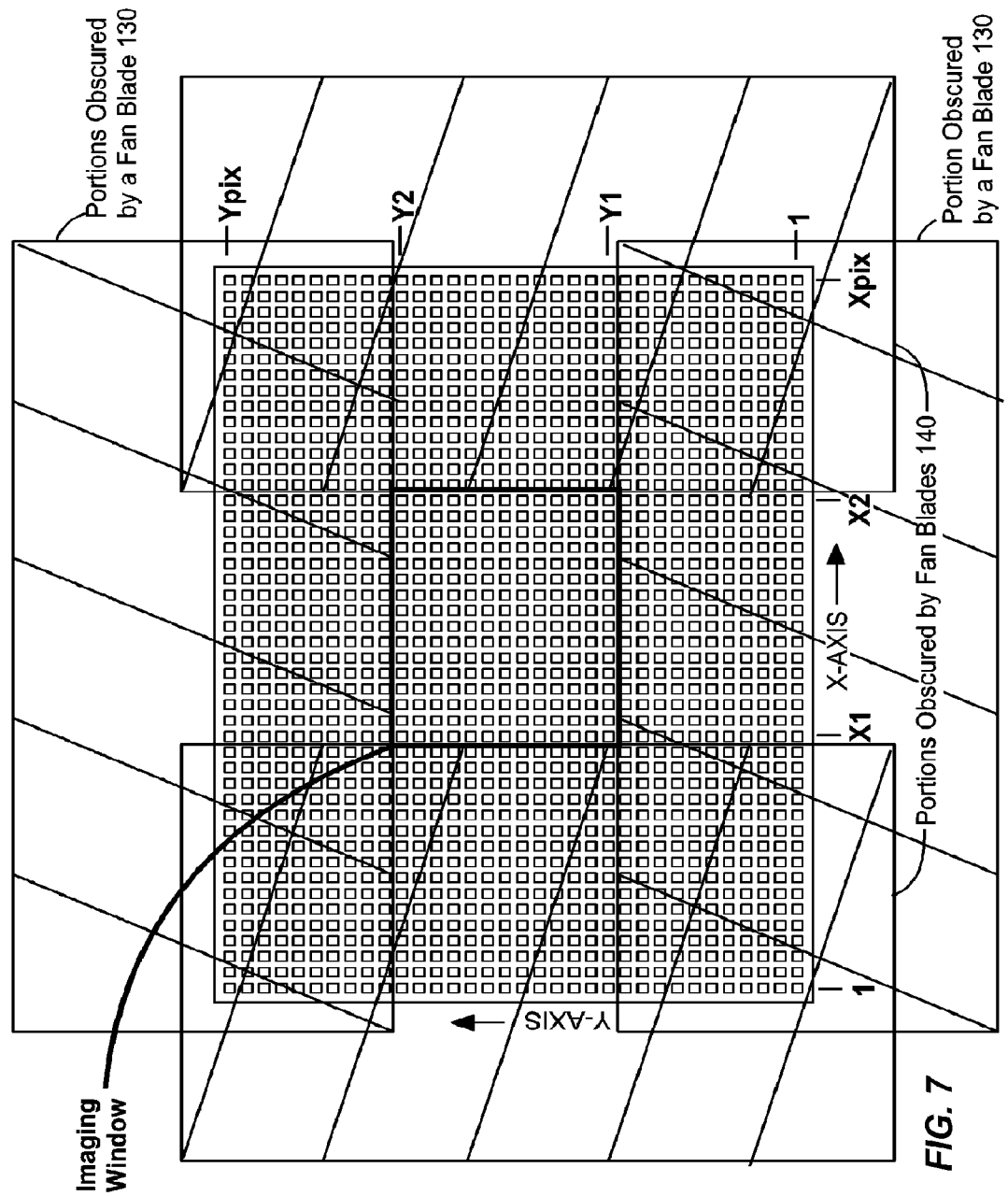

Each fan blade 130 and 140 is disposed closer to radiation source 110 than imaging device 120, and is adapted to significantly attenuate the radiation that strikes it, and to preferably substantially block it. The distal edges of fan blades 130 are preferably parallel to the X-axis of imaging device 120 and are selectively moveable, by way of fan blade drive 135, to obscure one or both sides of the cone-beam along the axial dimension. An example of the obscuring action is shown in FIG. 5, where pixels having Y coordinate values less than Y1 and greater than Y2 are substantially shielded from the radiation emitted by source 110, where Y1<Y2, and where both Y1 and Y2 are greater than 1 and less than Ypix. This is typically the preferred obscuring configuration, and leaves an imaging window through which direct-path radiation from source 110 may be received. The window is defined by the four points: (1,Y1), (1,Y2), (Xpix,Y1), and (Xpix,Y2). Similarly, the distal edges of fan blades 140 are preferably parallel to the Y-axis of imaging device 120 and are selectively moveable, by way of fan blade drive 145, to obscure one or both sides of the cone-beam along the trans-axial dimension. An example of the obscuring action is shown in FIG. 6, where pixels having X coordinate values less than X1 and greater than X2 are substantially shielded from the radiation emitted by source 110, where X1<X2, and where both X1 and X2 are greater than 1 and less than Xpix. This leaves an imaging window through which direct-path radiation from source 110 may be received, where the window is defined by the four points: (X1,1), (X1,Ypix), (X2,1), and (X2,Ypix). FIG. 7 shows an example where both sets of fan blades are positioned to obscure portions of the imaging device, leaving an imaging window through which direct-path radiation from source 110 may be received. The window is defined by the four points: (X1,Y1), (X1,Y2), (X2,Y1), and (X2,Y2). In preferred embodiments, controller 160 can send control signals to fan-blade drives to select any location and size of window desired by the operator.

Referring back to FIG. 2A, when controller 160 receives a request from the user to begin a scan of an object, controller 160 instructs fan-blade drives 135 and 145 to set the fan blades 130 and 140, respectively, in given positions (as described in greater detail below), instructs mechanical drive 155 to begin a scan rotation of gantry 150, and instructs radiation source 110 to begin emitting radiation. As it rotates, mechanical drive 155 provides controller 160 with an indication of the angular displacement value θ. Controller 160 uses this information to read the values of imaging device 120's pixel detectors at selected angular displacement values θ to obtain the data for the radiographic projections. Typically, there are between 250 and 1000 projections taken in the 360-degree scan rotation, with each projection being spaced from adjacent projections by a set increment Δθ of angular displacement. The controller stores the data from each projection in a memory storage device, along with the angular displacement value θ at which the projection was taken.

Controller 160 comprises a processor, an instruction memory for storing instruction sets that direct the operation of the processor, a data memory that stores pixel and other data values used by the present inventions implemented by the imaging system, and an I/O port manager that provides input/output data exchange between processor 160 and each of radiation source 110, mechanical drive 155, fan-blade drives 135 and 145, and imaging device 120. The instruction memory and data memory are coupled to the main processor through a first bidirectional bus, and may be implemented as different sections of the same memory device. Because of the large amount of data provided by the two-dimensional imaging device, the I/O port manager is preferably coupled to the main processor through a second bidirectional bus. However, the I/O port manager may be coupled to the main processor by way of the first bidirectional bus. The operation of the processor is guided by a group of instruction sets stored in the instruction memory, which is an exemplary form of computer-readable medium. Exemplary instruction sets are illustrated below.

In exemplary imaging system 100 shown in FIG. 2A, the gantry rotates about the object, which means that the projection line rotates about the object and the scan axis. Instead, it may be appreciated that the object and the scan axis may be rotated while the gantry and the projection line are stationary. A second exemplary imaging system which rotates the object is shown at 100' in FIG. 2B. System 100' comprises all of the components of system 100, with the components being coupled to one another in the same way, except that the mechanical drive is coupled to an object support member, which holds the object being scanned. In system 100', the gantry remains stationary while the mechanical drive rotates the object support member and the object. System 100' is suitable for industrial uses (e.g., scanning non-human objects), whereas system 100 is suitable for medical uses (e.g., scanning human objects).

Figure 8:
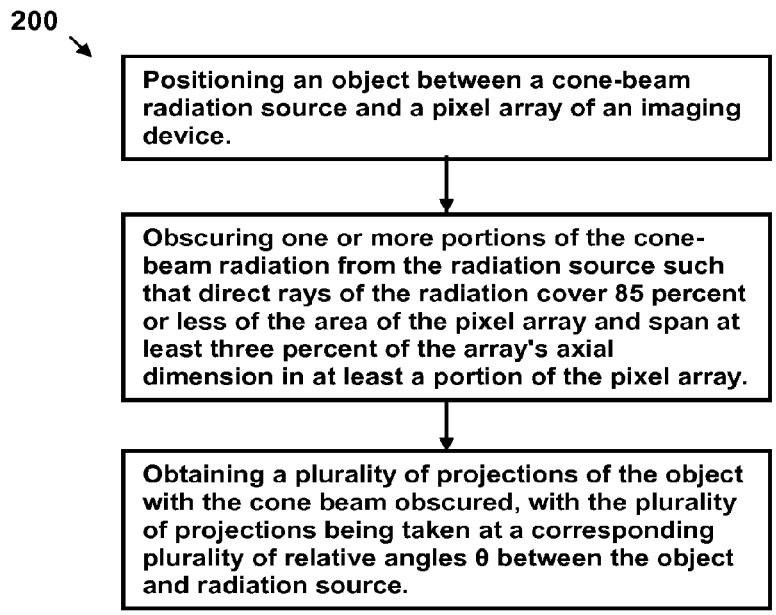
FIG. 8 shows a flow diagram of an exemplary embodiment of a method invention of the present application.

Methods and Computer-Program Products. A first general invention of the present application is directed to a method of operating a cone-beam CT scanning system, such as systems 100 and 100', and is illustrated by the flow diagram of an exemplary method 200 in FIG. 8. The exemplary method comprises positioning an object between the radiation source 110 and the imaging device 120, obscuring one or more portions of the cone-beam radiation from source 110 such that direct rays of the radiation cover 85 percent or less of the area of the pixel array and span at least three percent of the array's axial dimension (Y-axis) in at least a portion of the pixel array. These limitations can be stated mathematically as:

$$(X2-X1)*(Y2-Y1) \leq 0.85 * X\text{pix} * Y\text{pix}, \text{ and}$$

$$(Y2-Y1) \geq 0.03 * Y\text{pix over at least a portion of the } X\text{-axis.}$$

The obscuring action may be done before or after the positioning action. A lamp emitting visible light may be substantially co-located with radiation source 110 to facilitate performing the obscuring action by illuminating the imaging window onto the object support table before the positioning action, or onto the object during the positioning action. In typical implementations, the obscuring action is performed such that direct rays of the radiation span at least fifteen percent of the array's axial dimension (Y-axis) in at least a portion of the pixel array, and more typically at least twenty percent. Also, in many typical implementations, direct rays of the radiation may cover 75 percent or less of the area of the pixel array, and 50 percent or less. In some cases, it can be lower than 35 percent.

The exemplary method further comprises obtaining a plurality of projections of the object with the cone beam obscured, with the plurality of projections being taken at a corresponding plurality of relative angles θ between the object and radiation source 110. The number of projections is preferably sufficient to perform at least a truncated reconstruction of the voxel attenuation coefficients, being at least 250, preferably at least 400, more preferably at least 500, and most preferably at least 600. The actions of method 200 may be performed by an operator of system 100 (or 100'), such as a radiologist, physician, technologist, etc., and the projections may be stored in the data memory of controller 160. From there, the projections may be processed by a truncated reconstruction procedure to generate CT images of the imaged area of the object, as described below in greater detail, or may be exported to another data processor for processing.

Figure 9:
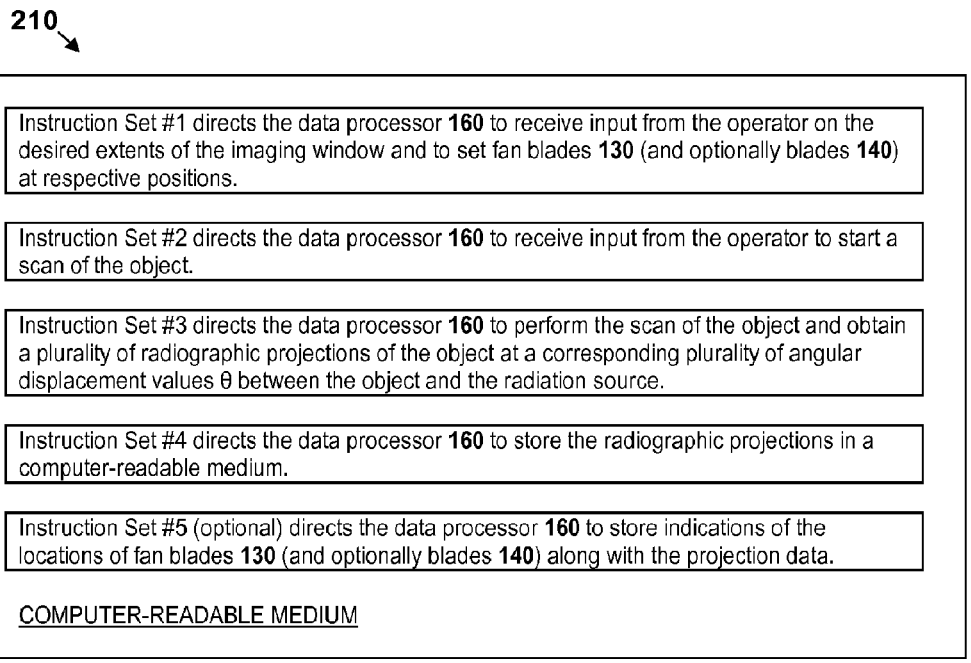
FIG. 9 shows an exemplary embodiment of a computer-program product invention of the present application.

To assist the operator with performing the above obscuring and obtaining actions, the instruction memory of data processor 160 may be loaded with an exemplary computer-program product 210 shown in FIG. 9. Product 210 comprises a computer-readable medium and a plurality of instruction sets embodied on the computer-readable medium. Instruction set #1 directs data processor 160 to receive input from the operator on the desired extents of the imaging window and to set fan blades 130 and 140 at respective positions. These instructions may include a subset of instructions that direct processor 160 to receive the values of the imaging window (e.g., the values of X1, X2, Y1, and Y2); they may include a subset of instructions that direct data processor 160 to provide a graphical representation of the pixel array of device 120 to the user, and to receive inputs from the user, such as in the form of mouse clicks, to define an imaging window on the graphical representation, and to draw a representation of the imaging window on the graphical representation. The subset of instructions may further direct the data processor 160 to receive inputs from the user to modify the position of the defined imaging window. In further embodiments, this subset of instruction set #1 may include instructions that direct data processor 160 to take a projection of the object (such as with θ=0), and to display the projection on the graphical representation. This enables the operator to identify features of the object, such as bones of a patient, and to locate the imaging window with respect to the identified features. The operator can also temporarily place radiation-absorbing markers on the object (e.g., patient) that indicate the desired extent of the imaging window during this initial projection. The markers will appear on the initial scan, and the operator can set the imaging window relative to the shown markers.

Instruction set #2 of product 210 directs data processor 160 to receive input from the operator to start a scan of the object. Instruction set #3 directs data processor 160 to perform the scan of the object and obtain a plurality of radiographic projections of the object at a corresponding plurality of angular displacement values θ between the object and the radiation source. Under the direction of instruction set #3, data processor 160 preferably instructs mechanical drive 155 to begin a scan rotation of gantry 150, instructs radiation source 110 to begin emitting radiation, receives indications of the angular displacement value θ from mechanical drive 155, and reads the values of imaging device 120's pixel detectors at selected angular displacement values θ to obtain the data for the radiographic projections. Instruction set #4 of computer-program product 210 directs data processor 160 to store the radiographic projections (i.e., pixel data and corresponding angular displacement value θ), in a computer-readable medium, such as the data memory of data processor 160, which may include a disk storage unit. Instruction set #4 may be performed in parallel with instruction set #3, storing each projection as it is read from imaging device 120. Product 210 may include an optional instruction set #5 that directs data processor 160 to store indications of the locations of fan blades 130 and 140 along with the projection data. This information can be stored as the extent of the imaging window (e.g., as X1, X2, Y1, and Y2), and can be useful to a truncation reconstruction procedure, which is described in greater detail below. However, the reconstruction procedure may comprise processing actions that deduce the extent of the imaging window, in which case the results of instruction set #5 are not needed.

Typically the operator wishes to set the imaging window to a target area of the object (e.g., patient), such as an organ of the patient, which is generally contained within a three-dimensional volume. It is important for the operator to recognize that the position of the object and the extent of the imaging window have to be collectively set so that the target volume is irradiated during the scan of the object. In one implementation, the values X1 and X2 are set to the full extent of the imager's x-dimension (X1=1 and X2=Xpix), and fan blades 130 are adjusted with the help of the previously described illumination lamp to illuminate the desired cross-section of the object. Since the rays of the cone-beam radiation diverge, this action is generally sufficient to capture the target region as long as the scan axis runs through the object (the reader may visually verify this by looking ahead to FIG. 11). The position of the object support table and/or the height of the object over the table may be adjusted to bring the scan axis within the volume of the object. In another implementation, the object is positioned such that the target volume at θ=0 is centered on the scan axis, such as by adjusting the trans-axial position of the object to center the lateral extent of the target volume about the scan axis, and adjusting the height of the object support table to center the thickness of the target volume about the scan axis. In this case, the axial extent of the target volume need only be located within the axial extent of imaging device 120. However, if desired and if possible, the axial position of the object may be adjusted so as to center the axial extent of the target volume about the position of the projection axis at θ=0. These adjustment actions may be done by the operator as a further embodiment of method 200, described above.

Once the target volume has been centered about the scan and projection axes, the extent of the imaging window may be determined as follows, and as illustrated by the trans-axial crosssection of the system shown in FIG. 10. The target area measures 2Δx by 2Δy by 2Δz, where Δx, Δy, and Δz can have different values, and where the dimension 2Δy is perpendicular to the page. In order to provide reconstructed voxel values in the target volume, the width of the imaging window in the X-dimension should be set to 2ΔX=2rD/d, where $r=[\Delta x^2 + \Delta z^2]^{1/2}$, where D is the shortest distance between radiation source 110 and imaging device 120, and where d is the distance between radiation source 110 and the scan axis. This can be deduced by applying geometric principles to the construction shown in the figure. X1 and X2 may then be set to X1=(Xpix/2−ΔX) and X2=(Xpix/2+ΔX). If it is not possible to center the x- and z-dimensions of the target value about the scan axis, then one may expand the size of the volume shown in the figure, in either one or both of the x- and z-dimensions, so as that the expanded volume encompasses the target volume, and then work with the expanded volume instead of the target volume. This approach can be taken when it is not possible to adjust the height of the object with respect to the support table.

Figure 11:
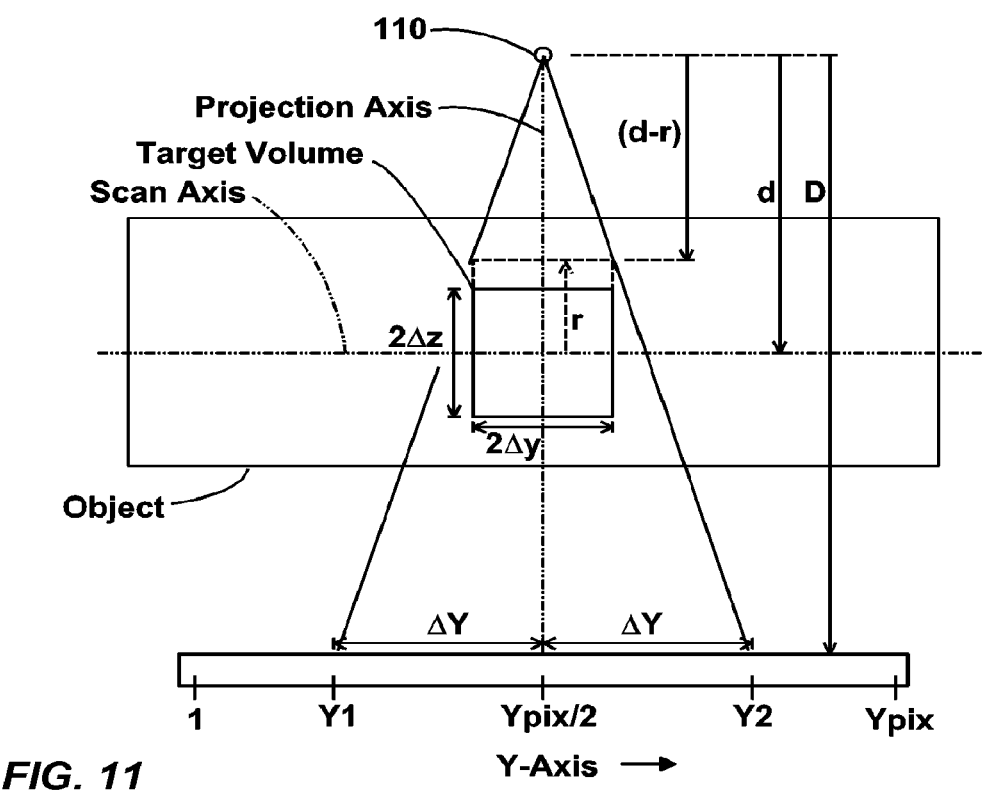

FIG. 11 shows the axial crosssection of the system with the target volume centered about the scan axis and the projection axis. During the scan of the object, there will be angles at which the some edges of the target volume will be at a distance of (d−r) from radiation source 110, as illustrated by dashed lines in the figure. In order to provide reconstructed voxel values in the target volume, the width of the imaging window in the Y-dimension should be set to 2ΔY=2ΔyD/(d−r), which can be deduced by applying geometric principles to the construction shown in the figure. Y1 and Y2 may then be set to Y1=(Ypix/2−ΔY) and Y2=(Ypix/2+ΔY). The value of r may be based on the dimensions of the target volume, or the above-described expanded volume if it is not possible to center the target volume about the scan axis. If it is not possible or desirable to center the y-dimension of the target volume about the projection axis, an offset may be added to the Y1 and Y2 values. For example, if the y-dimension of the target value is offset by a value Δb from the projection axis, then a value of ΔB may be added to both Y1 and Y2, such as Y1=(Ypix/2−ΔY+ΔB) and Y2=(Ypix/2+ΔY+ΔB), where ΔB=ΔbD/(d−r). Δb has a positive value when the target volume is offset toward Y=Ypix, and a negative value when the target volume is offset toward Y=1. As a point of generality, we may refer to the point (Xpix/2,Ypix/2) as (Xc,Yc), where the latter is defined as the point where the projection axis intersects the pixel array. If y1 and y2 are the extend of the target volume, as measured relative to the center point where the projection axis and scan axis intersect, then Δy may be generated as the absolute value of the difference between y1 and y2, and Δb may be generated as (y1+y2)/2.

Instruction set #1 of product 210 described above may comprise a subset of instructions that receives the extent of the target volume from the operator and computes the values X1, X2, Y1, and Y2 of the imaging window. The extent of the x- and y-dimensions of the target volume may be input by numeric values relative to a predefined measuring point, or may be obtained through the above-described graphical interface that shows the user an initial projection at θ=0 and enables the user to define a box on the graphical interface (the subset of instructions may then back-project the box to the plane of the scan axis using simple geometric operations). The z-dimension may be input as numeric values relative to the top of the object support table by the operator, and corrected for the distance between the scan axis and the table top. In some implementations, the subset of instructions may take a second projection of the object at θ=90, and provide the operator with a graphic representation of the second projection and graphic interface that enables the operator to define the z-dimension (the subset of instructions may then back-project this input to the plane of the projection axis using simple geometric operations). With this information, the subset of instructions may expand the target volume to account for any off-centering of the target volume, and then compute the image window with the actions previously described above.

Figure 10:
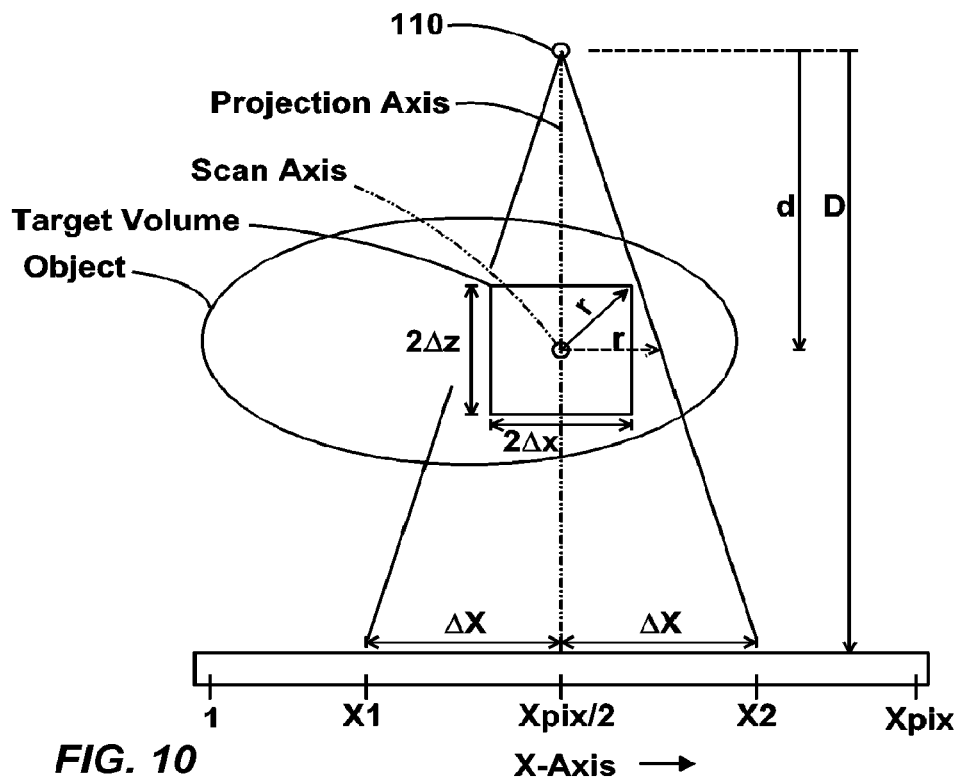
FIGS. 10 and 11 illustrate the determination of an image window from a target volume of an object according to an invention of the present application.
Figure 12:
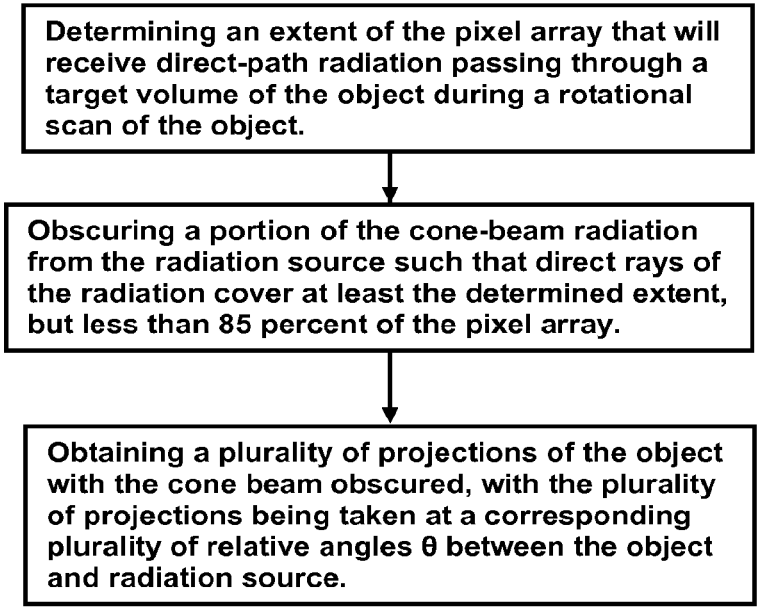
FIG. 12 shows a flow diagram of an exemplary embodiment of another method invention of the present application.

The paragraphs describing FIGS. 10 and 11 illustrated various actions that can be taken to determine (e.g., find) the extent of the pixel array that will receive direct-path radiation passing through a target volume of the object during a rotational scan of the object. This determination action actually comprises a part of another invention of the present application, which is described next with reference to the method flow diagram illustrated in FIG. 12. This invention relates to a method of operating a cone-beam CT scanning system, such as systems 100 and 100', which is illustrate by exemplary method 220 (FIG. 12). Method 220 comprises determining an extent of the pixel array that will receive direct-path radiation passing through a target volume of the object during a rotational scan of the object, the rotation scan including a plurality of projections of the object taken at a corresponding plurality of relative angles between the object and the source of radiation, the extent of the angles preferably being equal to or greater than 180 degrees, and the target portion being smaller than the size of the object. The extent may be determined by taking actions described in the three previous paragraphs. Method 220 further comprises obscuring one or more portions of the cone beam of radiation such that direct rays of the radiation cover at least the determined extent, but 85 percent or less of the pixel array. The obscuring action may be done by placing a collimator and/or one or more fan blades (e.g., fan blades 130 and/or 140) between the radiation source and the object. This action typically further comprises providing an imaging window in which the direct rays span at least three percent of the array's axial dimension, and more typically at least 15 to 20 percent of the array's axial dimension. Also, in many typical implementations, direct rays of the radiation may cover 75 percent or less of the area of the pixel array, and 50 percent or less. In some cases, it can be lower than 35 percent.

The exemplary method 220 further comprises obtaining a plurality of projections of the object with the cone beam obscured, with the plurality of projections being taken at a corresponding plurality of relative angles θ between the object and radiation source 110. The number of projections is preferably sufficient to perform at least a truncated reconstruction of the voxel attenuation coefficients. The actions of method 220 may be performed by an operator of system 100 (or 100'), such as a radiologist, physician, technologist, etc., and the projections may be stored in the data memory of controller 160. From there, the projections may be processed by a truncated reconstruction procedure to generate CT images of the imaged area of the object, as described below in greater detail, or may be exported to another data processor for processing.

Truncated reconstruction methods have been widely developed and used in the art for the case where the object is larger than the area of the two-dimensional imaging device. While these truncated reconstruction methods were not developed with the present inventions in mind, they may be readily adapted to process the projection data collected by the present inventions without undue experimentation by those of ordinary skill in the art. Papers and patents describing truncated reconstruction methods can be readily located by searching the Internet and free-access patent databases with the search terms "truncated reconstruction" and "tomography." U.S. Pat. Nos. 5,640,436 and 6,542,573, and published PCT application WO-2005-104038 A1 provide examples of truncated reconstruction methods, and are incorporated herein by reference.

Figure 13:
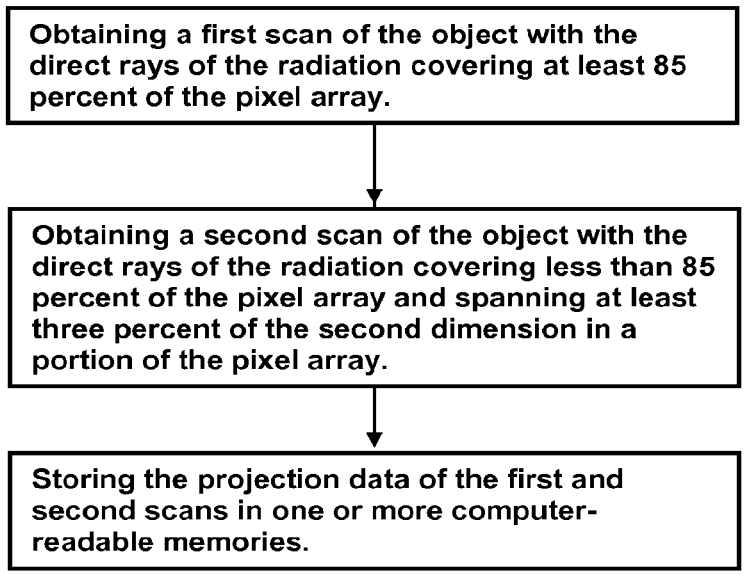
FIG. 13 shows a flow diagram of an exemplary embodiment of yet another method invention of the present application.

Yet another general invention of the present application is directed to a method of operating a cone-beam CT scanning system, such as systems 100 and 100', the system having a two-dimensional pixel array with a number Xpix of pixels in a first dimension that is preferably perpendicular to the system's axis of rotation and a number Ypix of pixels in a second dimension that is preferably parallel to the system's axis of rotation, Xpix being greater than one hundred and Ypix being greater than ten. The method is illustrated at 240 in FIG. 13, and comprises obtaining a first scan of the object with the direct rays of the radiation covering at least 85 percent of the pixel array, and obtaining a second scan of the object with the direct rays of the radiation covering less than 85 percent of the pixel array and spanning at least three percent of the second dimension in a portion of the pixel array. This action typically further comprises providing an imaging window in the second scan in which the direct rays span at least three percent of the array's axial dimension, and more typically at least 15 to 20 percent of the array's axial dimension. Also, in many typical implementations, direct rays of the radiation in the second scan may cover 75 percent or less of the area of the pixel array, and 50 percent or less. In some cases, it can be lower than 35 percent. The first and second scans may be performed in any order, and they may be performed in succession without having the object move from the support table, or they may be performed with a sufficiently long span of time, such as on different days, to allow the object to be away from the support table for a period of time. The projection data may be stored in a computer-readable medium. This action may be performed in an interleaved manner, with a portion of the action being performed after each scan, or contemporaneously with each scan. Further preferred embodiments of this method may include generating a three-dimensional CT data set from these projections using a truncated reconstruction method, as described below in greater detail. Data of the first scan may be used to estimate the missing data of the second scan. The obscured regions of either or both of the first and second scans may be used to generate estimates of the scattered radiation (as described below in greater detail), and these estimates may be subtracted out of the projection data, or otherwise factored out, prior to the reconstruction procedure.

Figure 14:
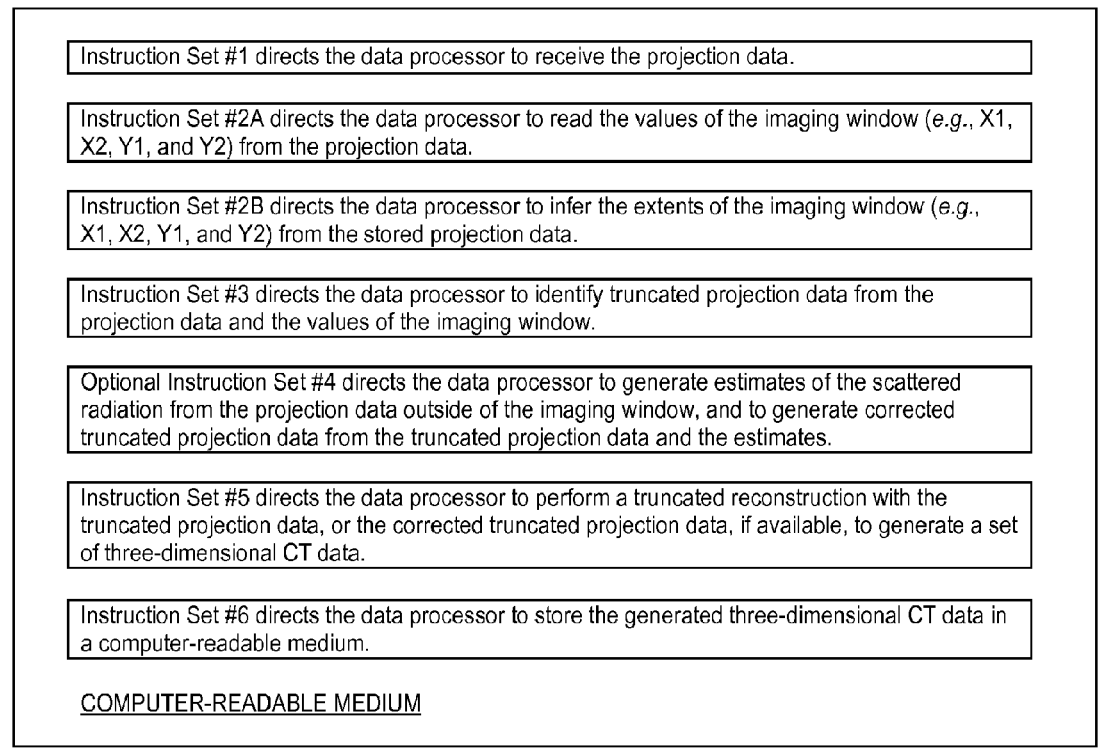
FIG. 14 shows an exemplary embodiment of another computer-program product invention of the present application.

Reconstruction Computer-Program Products. Related to the above inventions are a plurality of computer-program product inventions related to reconstructing three-dimensional CT data (e.g., voxels) from the two-dimensional projection data collected above. These products are described next. A first exemplary product is shown at 300 in FIG. 14. Product 300 comprises a computer-readable medium and a plurality of instruction sets embodied on the computer-readable medium, as shown in the figure. Instruction set #1 directs the data processor to acquire the projection data that was collected in the above-described inventions, such as by methods 200 and 220. In one embodiment, the instruction set may direct the data processor to receive the data, such as by reading it from a computer-readable medium. In another embodiment, product 300 may be loaded onto controller 160 and this instruction set may direct the data processor of controller 160 to instruct system 100 (or 100') to obtain the projection data. Typically, product 300 only uses one of instruction sets 2A and 2B, and may only comprise one or the other. Instruction set #2A directs the data processor to read the values of the imaging window (e.g., X1, X2, Y1, and Y2) from the stored projection data. Instruction set #2B directs the data processor to infer the extents of the imaging window (e.g., X1, X2, Y1, and Y2) from the stored projection data. This may be done by detecting the step change in pixel value that occurs at the boundaries of imaging window, such as convolving one or more of the projections with the sum of two orthogonal spatial derivative operators, which essentially generate the sum of dF/dx+dF/dy, where F represents the pixel data, and thereafter least-squares fitting four lines to the convolved data. It may also be done by a histogram analysis of the data to identify the group of pixels within the imaging window by their high value, differentiating them from the pixels outside the window by their low value, and then fitting a rectangle to pixels found to be within the window.

Instruction set #3 directs the data processor to identify truncated projection data from the projection data and the values of the imaging window, as found by instruction set #2A or #2B. Instruction set #3 may create arrays of the truncated data, and copy the pixel values within the imaging window to the new array for each projection. It may also merely set index ranges to the full projection data, to which further instructions may refer. As an option component of product 300, instruction set #4 directs the data processor to generate estimates of the scattered radiation from the projection data outside of the imaging window, and to generate corrected truncated projection data from the truncated projection data and the estimates. Exemplary instructions for this are described in a dedicated section below.

Instruction set #5 directs the data processor to perform a truncated reconstruction with the truncated projection data, or the corrected truncated projection data, if available, to generate a set of three-dimensional CT data. These instructions may implement the methods described in U.S. Pat. Nos. 5,640,436 and 6,542,573, or similar methods found in the art. The particulars of the reconstruction are not essential to the invention of product 300. Instruction set #6 directs the data processor to store the generated three-dimensional CT data in a computer-readable medium. From the three-dimensional CT data, a number of crosssections of the target volume may be constructed. Product 300 may comprise additional instruction sets that receive input from an operator to select a cross-section for display, and that in turn display the requested crosssection. The particulars of such crosssection display instructions are not essential to the invention of product 300. Product 300 may be run by data processor 160 (shown in FIGS. 2A and 2B), or another data processor.

Figure 15:
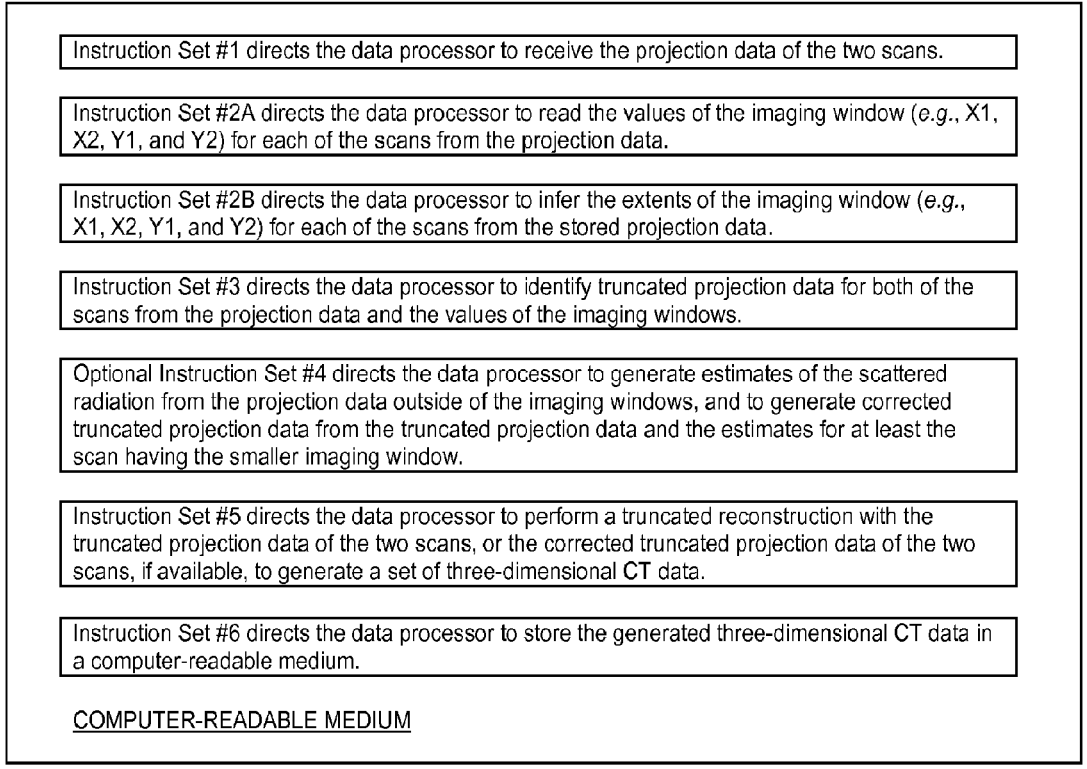
FIG. 15 shows an exemplary embodiment of yet another computer-program product invention of the present application.

A second general reconstruction product is illustrated by the exemplary produce 340 shown in FIG. 15. Product 340 comprises a computer-readable medium and a plurality of instruction sets embodied on the computer-readable medium, as shown in the figure. It is similar to product 300, but is intended to process the dual-scan data collected by method 240, described above. Instruction set #1 directs the data processor to acquire the projection data that was collected with method 240, or the like, from the appropriate computer-readable mediums. In one embodiment, the instruction set may direct the data processor to receive the data, such as by reading it from a computer-readable medium. In another embodiment, product 300 may be loaded onto controller 160 and this instruction set may direct the data processor of controller 160 to instruct system 100 (or 100') to obtain the projection data. Instruction set #2A directs the data processor to read the values of the imaging window (e.g., X1, X2, Y1, and Y2) for each of the scans from the stored projection data. Instruction set #2B directs the data processor to infer the extents of the imaging window (e.g., X1, X2, Y1, and Y2) for each of the scans from the stored projection data. This may be done as described above for method 300, the actions of which are incorporated herein by reference. Typically, product 340 only uses one of instruction sets 2A and 2B, and may only comprise one or the other.

Instruction set #3 directs the data processor to identify truncated projection data for both of the scans from the projection data and the values of the imaging window, as found by instruction set #2A or #2B. Instruction set #3 may create arrays of the truncated data, and copy the pixel values within the imaging window to the new array for each projection. It may merely set index ranges to the full projection data, to which further instructions may refer. As an option component of product 340, instruction set #4 directs the data processor to generate estimates of the scattered radiation from the projection data outside of the imaging window, and to generate corrected truncated projection data from the truncated projection data and the estimates. This is preferably done for both scans. Exemplary instructions for this are described in a dedicated section below. If the imaging window for the scan of the larger pixel area covers the entire pixel array, this step is omitted for the larger-area scan, or is modified to use estimates from the smaller-area scan. Instruction set #5 directs the data processor to perform a truncated reconstruction with the truncated projection data, or the corrected truncated projection data, if available, to generate a set of three-dimensional CT data. These instructions may implement the methods described in published PCT application WO-2005-104038 A1, or similar methods found in the art. The method essentially finds where each projection of the smaller-area scan matches the corresponding projection of the larger-area scan (which may be done by a two-dimensional auto-correlation of the original data or the scatter-corrected data), and then replaces the data of the larger-area scan in the matched area with the corresponding data of the smaller-area scan, in the matched area. The particulars of the reconstruction are not essential to the invention of product 340. Instruction set #6 directs the data processor to store the generated three-dimensional CT data in a computer-readable medium. From the three-dimensional CT data, a number of crosssections of the target volume may be constructed. Product 340 may comprise additional instruction sets that receive input from an operator to select a crosssection for display, and that in turn display the requested crosssection. The particulars of such crosssection display instructions are not essential to the invention of product 340. Product 340 may be run by data processor 160 (shown in FIGS. 2A and 2B), or another data processor.

It may be appreciated that each of the above computer-program products performs a corresponding method, which may be separately recited herein as a set of independent and dependent method claims.

Figure 16:
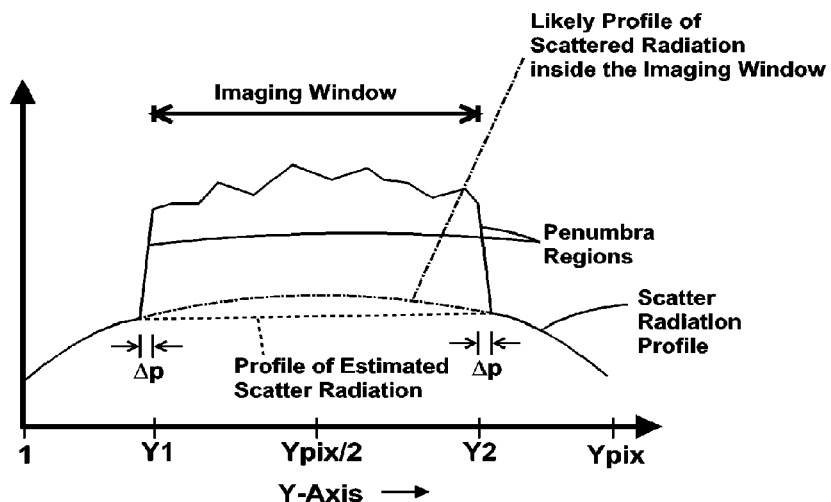
FIG. 16 shows a cross section through an imaging window to illustrate how scattered radiation may be estimated according to some inventions of the present application.

Scatter-Estimation Methods and Computer-Program Products. FIG. 16 shows the pixel values of an axial line of pixels from Y1 to Ypix for some value of X that crosses through the imaging window. Image data and scattered radiation are present within the imaging window (the scattered radiation being much less compared to the case of a full-width imaging window), and scatter radiation is present at the extremes of the axial line (near Y=1 and Y=Ypix). At the edges of the imaging window, there are transition regions due to the penumbra of radiation source 110. As is know in the art, the source is not a perfect point, but has some width. This width interacts with the edges of fan blades 130 to create a tapering of the incident radiation, rather than a step change, and this tapering causes tapered regions of width $\Delta p$ between the edges of the imaging window and the scatter radiation profiles at the extremes. The likely profile of the scattered radiation within the imaging window can be estimated by human eye as the dot-dashed line shown in the figure. A good estimate of the likely profile can be generated at the dashed straight line, which is constructed as a straight line from two pixel values just outside of the two penumbra regions, such as at $(Y1-\Delta p)$ and $(Y2+\Delta p)$. This is a simple linear interpolation form. More complex interpolation forms may be used, such as splines. Because the pixel data often has spurious noise, it is preferred to average the value of $(Y1-\Delta p)$ with the corresponding values of adjacent axial lines, and to average the value of $(Y2+\Delta p)$ with the corresponding values of adjacent axial lines, before constructing the interpolation. This will lessen the effects of spurious noise. This interpolation may be done for each axial line traversing the imaging window. While the above methods of estimating the scatter radiation have been done along the axial lines, it may be done along the trans-axial lines as well, particularly if the trans-axial width of the imaging window is narrower than the axial width of the imaging window.

Once the estimates of the scatter radiation inside the imaging window are generated by such an interpolation, they may be subtracted directly from the corresponding pixel values in the imaging window to generate corrected projection data. However, because of possible spurious noise, it may be preferred to perform a truncated subtraction rather than a direct subtraction. The truncated subtraction is generated by forming the ratio between the scatter estimate for a pixel and the pixels value, limiting the maximum value of this ratio to a predetermined ceiling value a that represents a reasonable expected upper bound for scattering ratio, multiplying the limited ratio by the pixel's value, and thereafter subtracting the resulting multiplication from the pixel value. This may be mathematically expressed as $PVc=PV-PV*\text{limit}(SE/PV, \alpha)$, where PVc is the scatter-corrected pixel value, PV is the pixel value, SE is the scatter estimate for the pixel, and limit(*,*) is the limit function.

Figure 17:
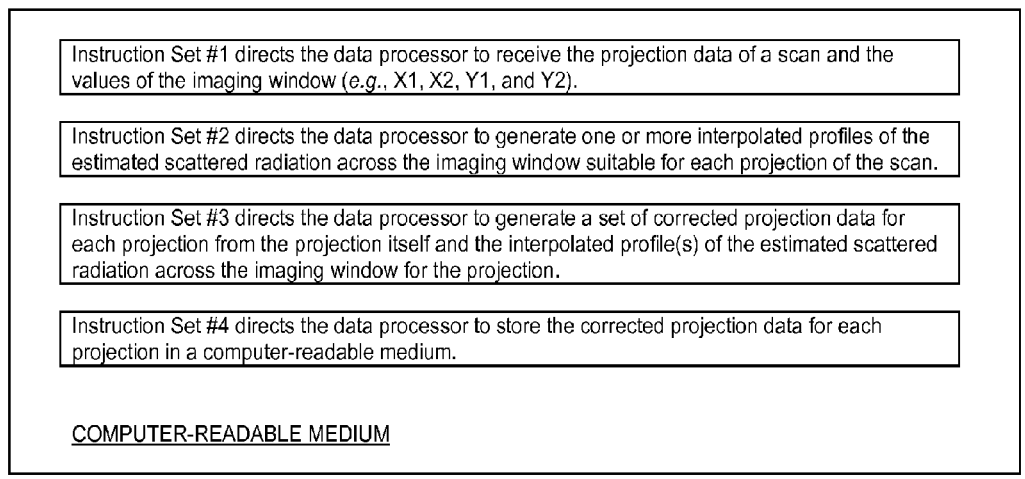
FIG. 17 shows an exemplary embodiment of yet another computer-program product invention of the present application.

In view of the above discussion, an exemplary computer-program product 400 for scatter correction is provided in FIG. 17. Product 400 is suitable for stand-alone use or use with products 300 and 340 as instruction set #4. Product 400 comprises a computer-readable medium and a plurality of instruction sets embodied on the computer-readable medium, as shown in the figure. Instruction set #1 directs the data processor to acquire the projection data of a scan and the values of the imaging window (e.g., X1, X2, Y1, and Y2). In one embodiment, the instruction set may direct the data processor to receive the data, such as by reading it from a computer-readable medium. In another embodiment, product 400 may be loaded onto controller 160 and this instruction set may direct the data processor of controller 160 to instruct system 100 (or 100') to obtain the projection data. Instruction set #2 directs the data processor to generate one or more interpolated profiles of the estimated scattered radiation across the imaging window suitable for each projection of the scan.

Instruction set #2 preferably includes averaging pixel values outside of the imaging window, and generating the interpolations from the averaged values. Product 400 includes instructions embodied on the computer-readable medium that directs the data processor to store the estimates of the scattered radiation on a computer-readable memory. Instruction set #3 directs the data processor to generate a set of corrected projection data for each projection from the projection data itself and the interpolated profile(s) of the estimated scattered radiation across the imaging window for the projection. This may be generated as a direct subtraction of the estimated scatter profile from the pixel values, or as the truncated subtraction of the estimated scatter profile from the pixel values, as described above. Instruction set #4 directs the data processor to store the corrected projection data for each projection in a computer-readable medium.

It may be appreciated that the above computer-program products perform corresponding methods, which may be separately recited herein as sets of independent and dependent method claims.

For projection data collected from method 240 for the large-area scan, if the imaging window covers the entire area of the large area scan, then the interpolation profiles of estimated scattered radiation generated for each projection of the small-area scan may be applied to the corresponding projection of the large area scan, with the profiles being extrapolated to the regions outside of the imaging window, and optionally scaled by a factor greater than 1 to account for the additional radiation received by the object during the large area compared to the small area scan. (The additional radiation received by the object cases more scattered radiation in the large area scan than compared to the small area scan.)

The instruction sets of the above-described computer-program products may be combined together, either in whole or various sub-combinations, to provide additional computer-program products. The actions of the methods performed by the instruction sets may be similarly combined to provide additional methods.

Figure 18:
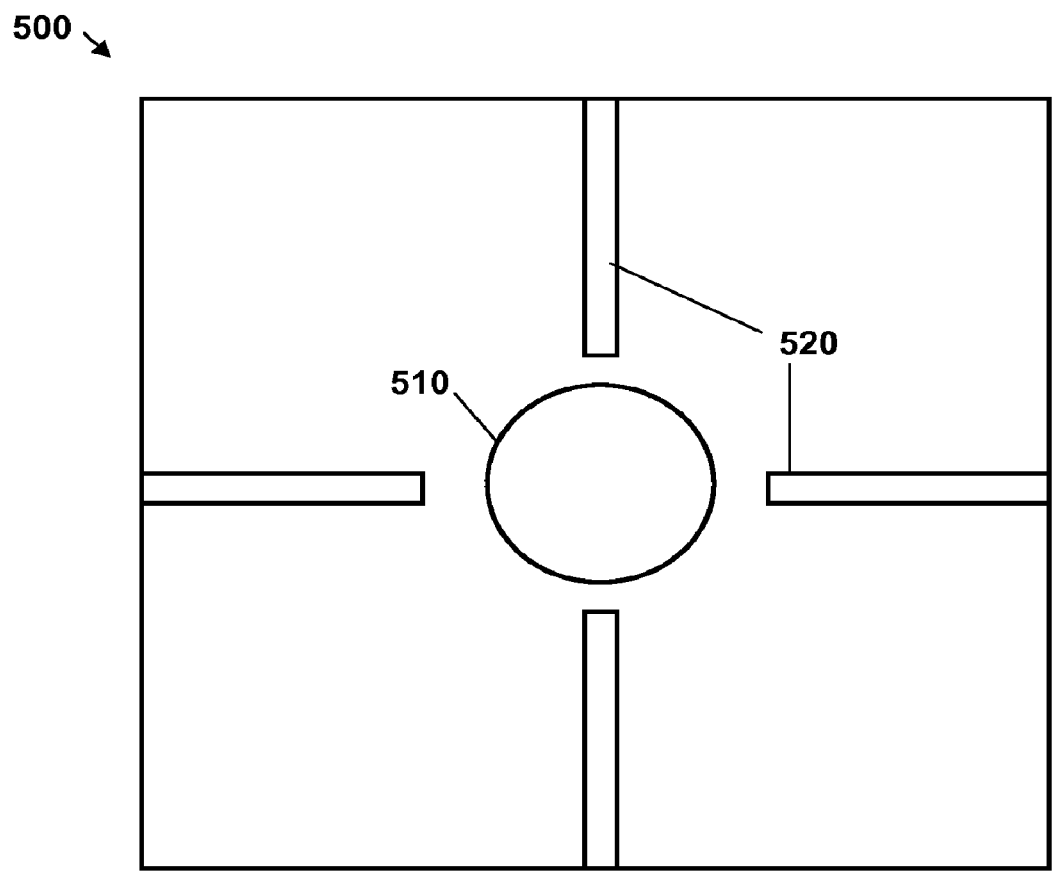
FIG. 18 shows an exemplary embodiment of a collimator invention of the present application.

Additional Collimator Structures. In addition to fan blades, the present inventions may be practiced with various collimator structures. An exemplary collimator structure 500 is shown in FIG. 18. It comprises a plate of radiation attenuation material, with the properties described above for fan blades 130 and 140, a central aperture 510 through the plate to allow radiation to pass without attenuation, and a plurality of slits 520 disposed along the axial and trans-axial dimensions, crossing at the center of aperture 510. Collimator 500 may replace fan blades 130 and 140 in systems 100 and 100', and may be moved in the axial and trans-axial directions by linear motor servos and the like. Collimator 500 produces a circular or oval-shaped image window on imaging device 120, and it may also be moved along the projection axis by another linear motor servo to vary the diameter of the image window. Slits 520 also allow radiation to pass through the plate without attenuation, and generate projection slices of the object which may be found and used by truncation reconstruction programs to better estimate the missing projection data. Slits 520 do not appreciably increase the scatter radiation. Slits 520 may be incorporated into fan blades 130 and 140.

Any recitation of "a", "an", and "the" is intended to mean one or more unless specifically indicated to the contrary.

As used herein, computer-readable medium includes, but is not limited to, volatile memory, such as a data memory of a data processor, non-volatile memory (such as EPROMs, EEPROMs, "jump drives"), magnetic disk drive storage (including fixed media and removable media), floppy disks, optical discs (such as CD-ROM discs and writable DVD discs), magnetic tape, optical tape, magnetic drums, optical drums, holograms, and any other tangible medium to which data may be written, and from which data may be read, at the request of a computer, microprocessor, data processor, and the like.

The pixel arrays used here preferably have X- and Y-dimensions of at least 100 pixels in each dimension, and more preferably at least 400 pixels in each dimension, and most preferably at least 700 pixels in each dimension.

The terms and expressions which have been employed herein are used as terms of description and not of limitation, and there is no intention in the use of such terms and expressions of excluding equivalents of the features shown and described, it being recognized that various modifications are possible within the scope of the invention claimed.

Moreover, one or more features of one or more embodiments of the invention may be combined with one or more features of other embodiments of the invention without departing from the scope of the invention.

While the present invention has been particularly described with respect to the illustrated embodiments, it will be appreciated that various alterations, modifications, adaptations, and equivalent arrangements may be made based on the present disclosure, and are intended to be within the scope of the invention and the appended claims.

What is claimed is:

1. A method of processing projection data that has been taken by a system, the system comprising a pixel array having a plurality of pixels and a radiation source that emits cone-beam radiation toward the pixel array, the method comprising:
    acquiring a set of radiographic projections of an object that has been taken by the system with a portion of the plurality of pixels being obscured from the cone-beam radiation, each radiographic projection having a plurality of pixel values corresponding to the plurality of pixels of the pixel array, each pixel value being representative of an amount of radiation received by its corresponding pixel for the projection;
    acquiring an indication of which pixels have been obscured; and
    generating estimates of scattered radiation from the pixel values of the obscured pixels.

2. The method of claim 1 wherein acquiring the set of radiographic projections of the object comprises receiving the set of radiographic projections.

3. The method of claim 1 wherein acquiring the set of radiographic projections of the object comprises obtaining the set of radiographic projections from a cone-beam CT system.

4. The method of claim 1 wherein acquiring an indication of which pixels have been obscured comprises receiving the indication.

5. The method of claim 1 wherein acquiring an indication of which pixels have been obscured comprises analyzing the pixel values to determine which pixels have been obscured.

6. The method of claim 1 wherein generating estimates of scattered radiation from the pixel values of the obscured pixels comprises generating an interpolation profile that spans at least some of the unobscured pixels of the set of radiographic projections.

7. The method of claim 1 wherein generating estimates of scattered radiation from the pixel values of the obscured pixels comprises generating two or more averages of pixel values of two or more groups of obscured pixels, and generating an interpolation profile from the two or more averages that spans at least some of the unobscured pixels of the projections.

8. The method of claim 1 further comprising generating a plurality of corrected projections from the set of radiographic projections and the estimates of the scattered radiation.

9. A computer-program product that directs a data processor to process projection data that has been taken by a system, the system comprising a pixel array having a plurality of pixels and a radiation source that emits cone-beam radiation toward the pixel array, the computer-program product comprising:

a non-transitory computer-readable medium;

a first set of instructions embodied on the computer-readable medium that directs a data processor to acquire a first set of radiographic projections of an object with a portion of the plurality of pixels being obscured from the cone-beam radiation, each radiographic projection having a plurality of pixel values corresponding to the plurality of pixels of the pixel array, each pixel value being representative of an amount of radiation received by its corresponding pixel for the projection;

a second set of instructions embodied on the computer-readable medium that directs the data processor to acquire an indication of which pixels have been obscured in at least the first set of radiographic projections; and a third set of instructions embodied on the computer-readable medium that directs the data processor to generate estimates of scattered radiation from the pixel values of the obscured pixels.

10. The computer-program product of claim 9 wherein the first set of instructions directs the data processor to obtain the first set of radiographic projections from a computer-readable medium.

11. The computer-program product of claim 9 wherein the first set of instructions directs the data processor to obtain the first set of radiographic projections from a cone-beam CT system.

12. The computer-program product of claim 9 wherein the second set of instructions directs the data processor to receive the indication of which pixels have been obscured comprises receiving the indication.

13. The computer-program product of claim 9 wherein the second set of instructions directs the data processor to analyze the pixel values to generate the indication of which pixels have been obscured.

14. The computer-program product of claim 13 wherein the second set of instructions directs the data processor to generate a histogram of the pixel values.

15. The computer-program product of claim 13 wherein the second set of instructions directs the data processor to convolve the pixel values of one of the radiographic projections of the first set of radiographic projections with a derivative operator.

16. The computer-program product of claim 9 wherein the third set of instructions directs the data processor to generate an interpolation profile that spans at least some of the unobscured pixels of the projections.

17. The computer-program product of claim 9 wherein the third set of instructions directs the data processor to generate two or more averages of pixel values of two or more groups of obscured pixels, and to generate an interpolation profile from the two or more averages that spans at least some of the unobscured pixels of the projections.

18. The computer-program product of claim 9 further comprising a fifth set of instructions that directs the data processor to generate a plurality of corrected projections from the first set of radiographic projections and the estimates of the scattered radiation.

* * * * *

UNITED STATES PATENT AND TRADEMARK OFFICE
CERTIFICATE OF CORRECTION

PATENT NO. : 8,320,518 B2
APPLICATION NO. : 13/209323
DATED : November 27, 2012
INVENTOR(S) : Larry Partain It is certified that error appears in the above-identified patent and that said Letters Patent is hereby corrected as shown below:

In the Claims:

In Column 22, Claim 12, Lines 7-8, please delete "comprises receiving the indication".

Signed and Sealed this
Ninth Day of April, 2013

Teresa Stanek Rea
*Acting Director of the United States Patent and Trademark Office*